(12) United States Patent
Fukaya et al.

(10) Patent No.: US 6,318,864 B1
(45) Date of Patent: *Nov. 20, 2001

(54) STERILE INSTRUMENTS COVER FOR USE ON SURGICAL MICROSCOPES

(75) Inventors: Takashi Fukaya, Sagamihara; Tohru Shinmura, Hachioji; Koji Yasunaga, Hino; Kazuo Banju, Hachioji; Masaaki Ueda, Hachioji; Tomonori Ishikawa, Hachioji; Hiroshi Fujiwara, Hachioji; Masanori Kaneda, Hachioji; Junichi Nozawa, Hachioji, all of (JP)

(73) Assignee: Olympus Optical Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/557,533

(22) Filed: Nov. 14, 1995

(30) Foreign Application Priority Data

Nov. 15, 1994 (JP) ........................................ 6-280297

(51) Int. Cl.⁷ ........................... B85D 85/38; B65D 65/02; G02B 21/00
(52) U.S. Cl. ........................... 359/510; 359/511; 359/368
(58) Field of Search .................................... 359/507, 510, 359/511, 513, 368, 372

(56) References Cited

U.S. PATENT DOCUMENTS

| | | | |
|---|---|---|---|
| 3,528,720 | * 9/1970 | Treace | 359/510 |
| 3,698,791 | * 10/1972 | Walchle et al. | 359/510 |
| 3,796,477 | 3/1974 | Geraci | 350/65 |
| 4,045,118 | * 8/1977 | Geraci | 359/510 |
| 4,183,613 | 1/1980 | Walchle et al. | 350/65 |
| 4,266,663 | * 5/1981 | Geraci | 359/510 |
| 4,561,540 | * 12/1985 | Hunter et al. | 359/510 |
| 4,799,779 | * 1/1989 | Mesmer | 359/510 |
| 5,036,446 | 7/1991 | Quintanilla et al. | 362/399 |
| 5,122,904 | 6/1992 | Fujiwara et al. | 359/510 |
| 5,355,292 | 10/1994 | Hoftman et al. | 362/400 |
| 5,467,223 | * 11/1995 | Cleveland, Jr. et al. | 359/510 |

FOREIGN PATENT DOCUMENTS 03-017493 B2   3/1991   (JP) .
6-196          1/1994   (JP) .

* cited by examiner

Primary Examiner—Ricky D. Shafer
(74) Attorney, Agent, or Firm—Morgan, Lewis & Bockius LLP

(57) ABSTRACT

A microscope for operation body 1 having an objective lens 4 and eyepieces 5 is combined with a cap that is capable of covering the entire part of the microscope body 1 and which is made of a sterilizable elastic material such as rubber. A retaining portion 7 projecting to retain the cap is provided on the microscope body 1 and a mounting portion engageable with the retaining portion 7 is provided on the cap.

43 Claims, 19 Drawing Sheets

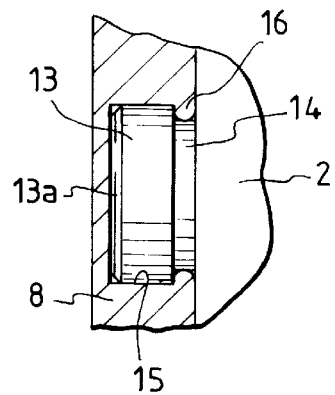
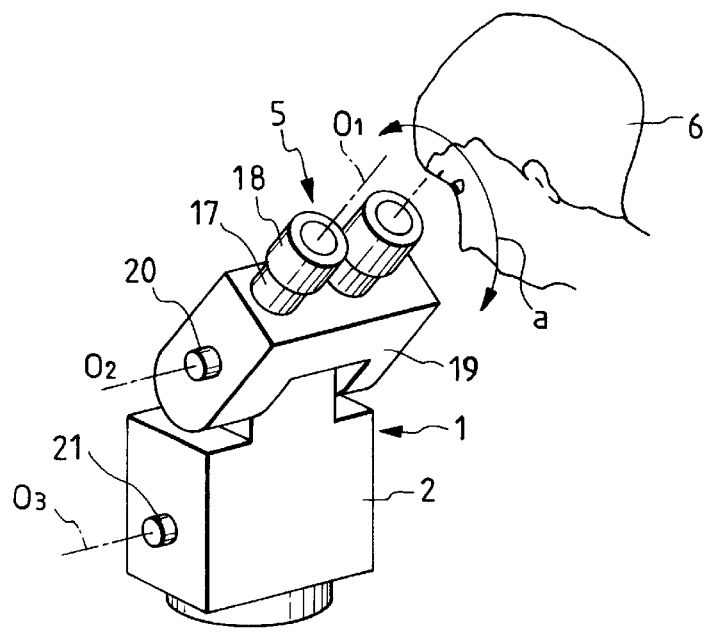
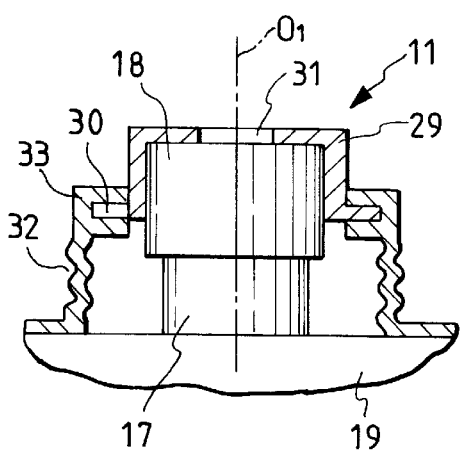
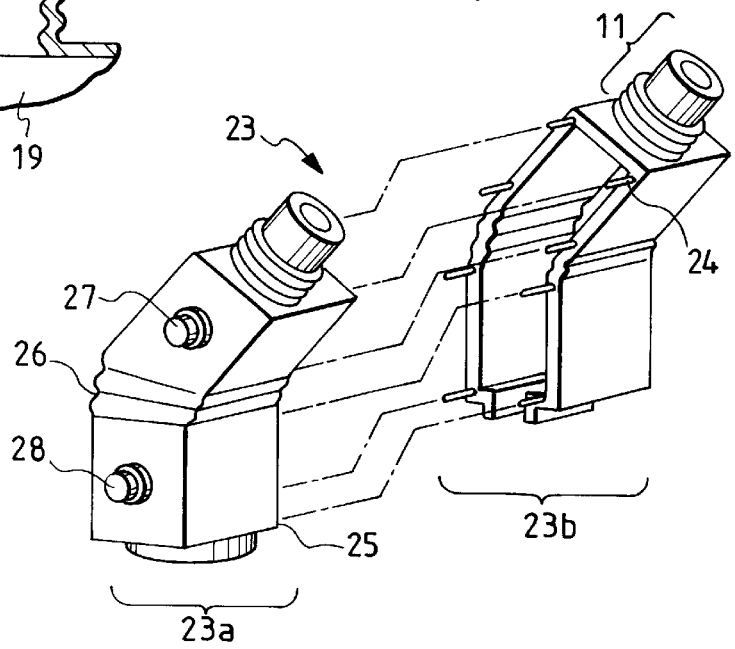

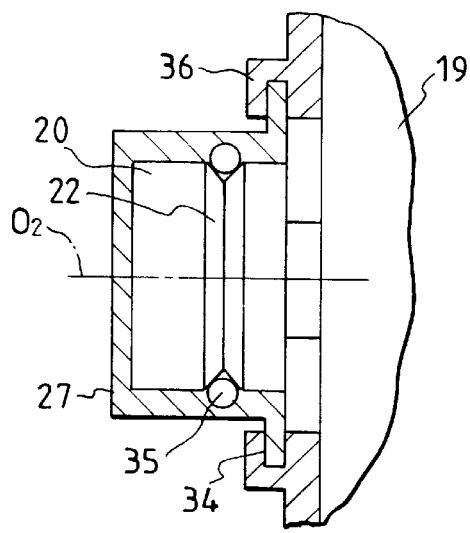
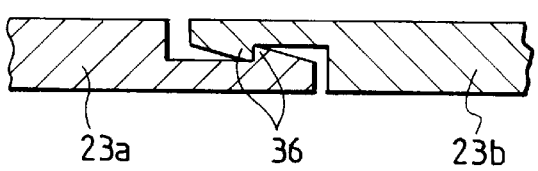
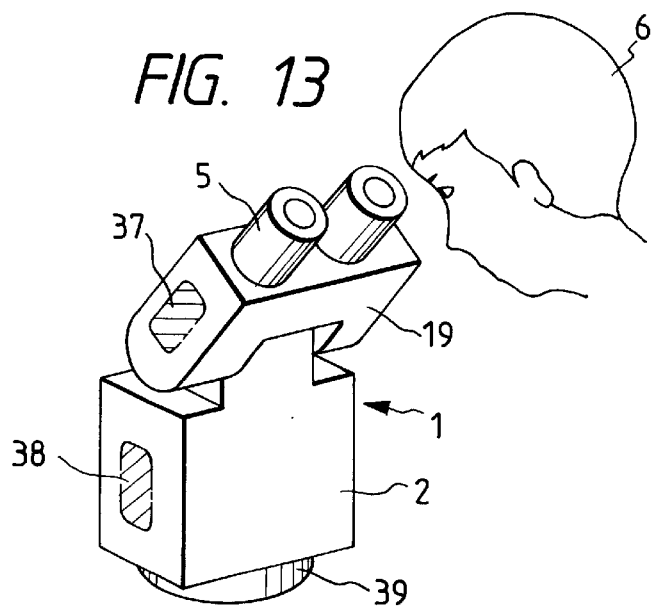
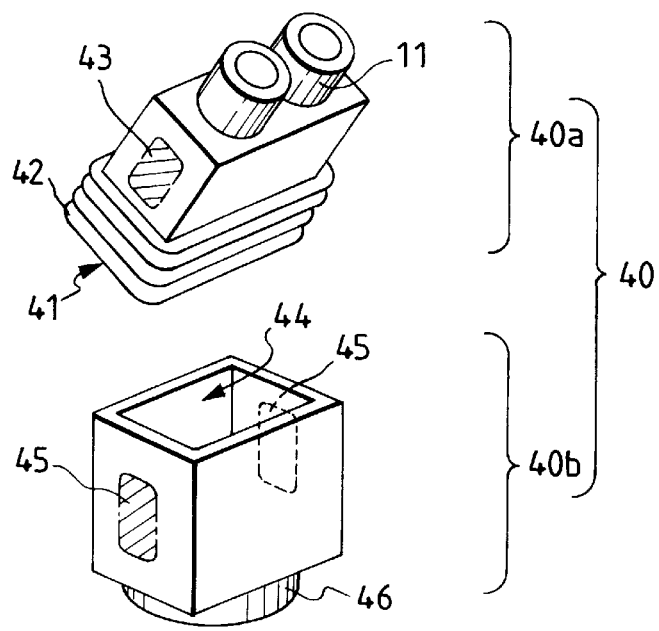

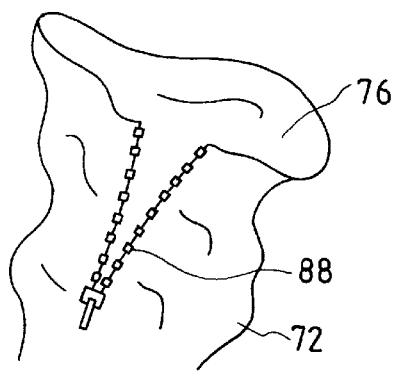
FIG. 23
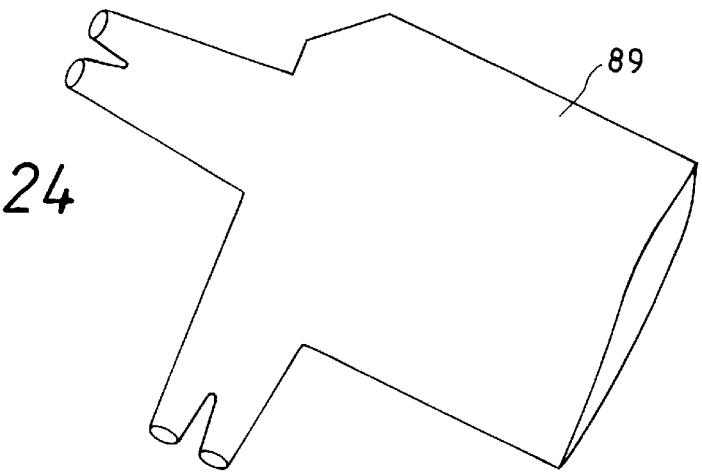
FIG. 24
FIG. 25
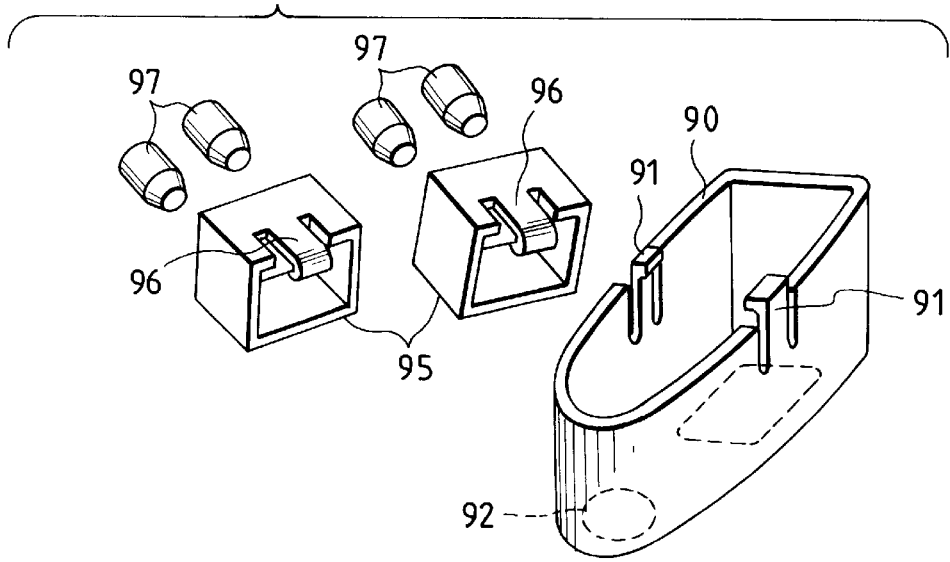

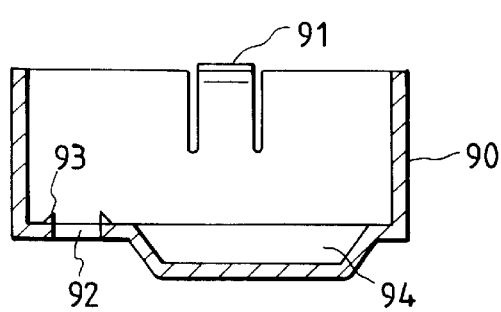
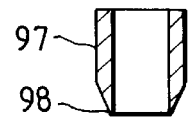
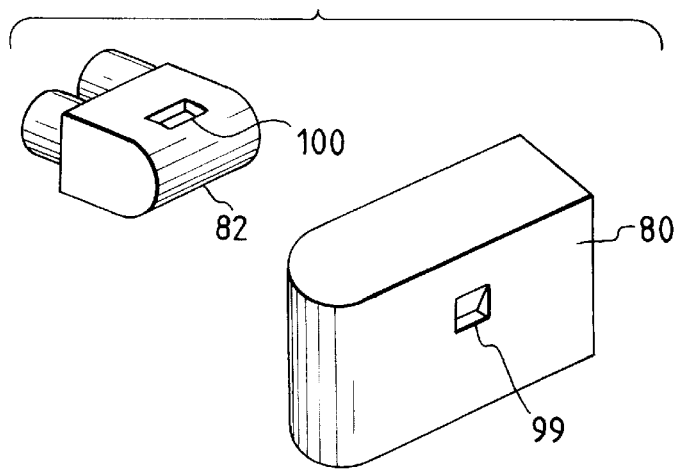
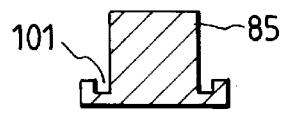
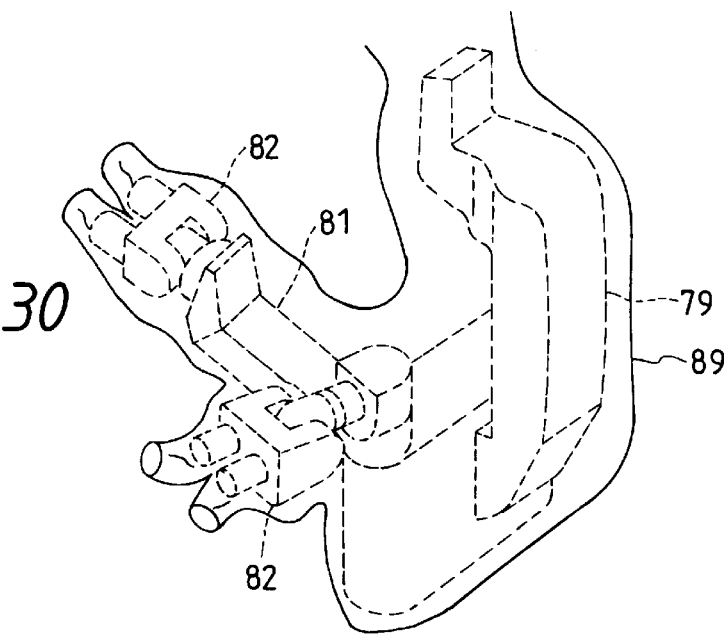

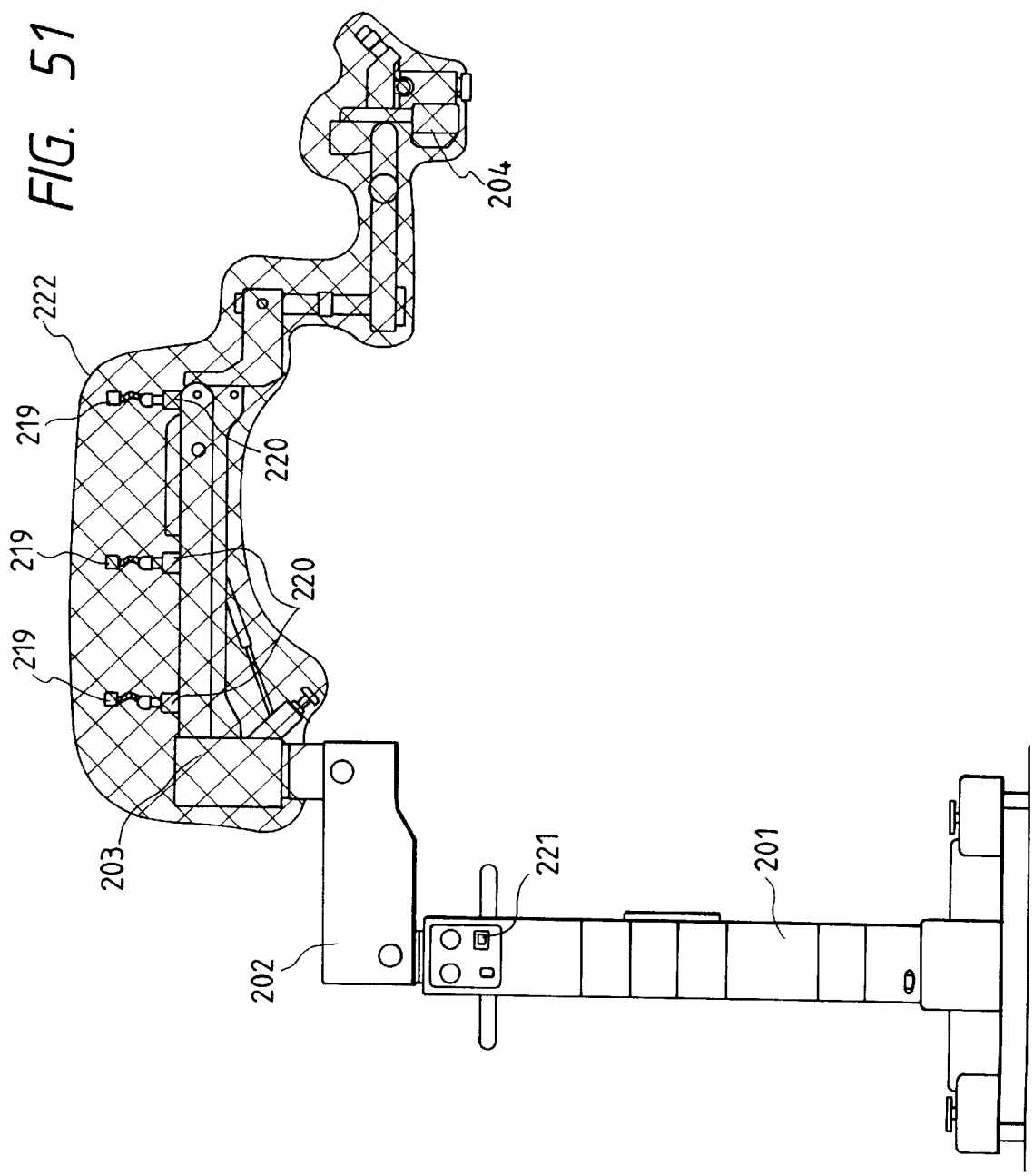

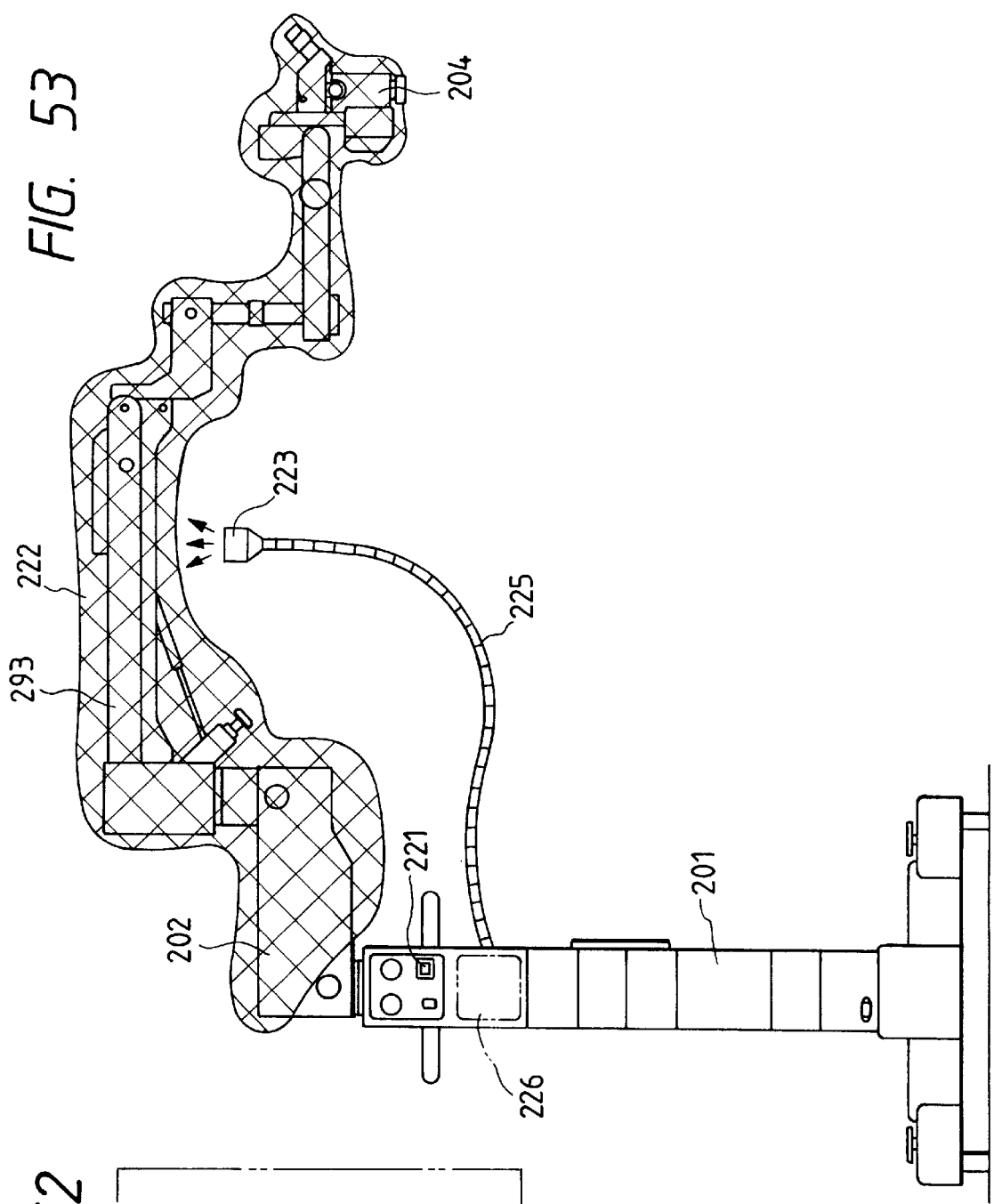
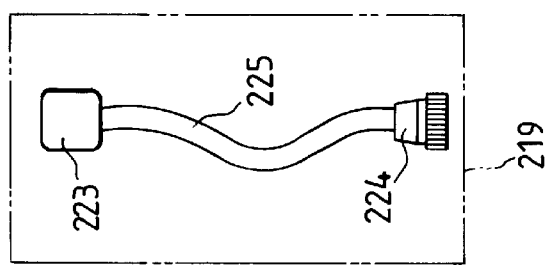

STERILE INSTRUMENTS COVER FOR USE ON SURGICAL MICROSCOPES

BACKGROUND OF THE INVENTION

1. Technical Field of the Invention

The present invention relates to sterile instruments for use with microscopes for operations in microsurgical, such as neurosurgical and orthapedic, operations.

2. Related Art

The recent advances in operating methods and instruments have made microsurgery a routine practice. In microsurgery, a microscope for operations is employed to examine, at an increased magnification, the part of a patient being operated on. A common method of sterilizing the microscope for operation is to cover it with an already sterilized drape so that its exterior portions are rendered in an aseptic condition.

To keep the surgeon in a sterile condition, a sterile cap may be mounted on those parts of a microscope for operation which an operator may manipulate during the surgical operation, and U.S. Pat. No. 5,036,446 proposed the use of a sterile cap for handling surgical lamps.

Turning back to the drape, it is dimensioned to be larger than the microscope for operation so that it can smoothly mount over the latter but that it will not degrade the manipulability of the enclosed microscope. After covering the microscope for operation, loose portions of the drape are usually gathered by rubber bands or tie strings and secured to support arms and the like of the microscope.

However, during actual use, the drape must have a certain allowance for permitting free movements of the moving parts of the microscope for operation but in the fixing method just described above, the degree of loosening of the drape has to be adjusted with the microscope being actually manipulated and this has been one of the reasons that a prolonged time is required in making preparations for a surgical operation. Furthermore, loose portions of the drape can interfere with the vision of the surgeon or they may accidentally contact nonsterilized parts. In addition, the drape is discarded after use but this only adds to the running cost of surgical operations.

The sterile cap described in U.S. Pat. No. 5,036,446 also is not problem-free. Those parts of the microscope for operation which are not covered with the cap are non-sterile and may accidentally be touched by the surgeon during the surgical operation. In addition, if more than one part of the microscope is to be manipulated, the sterile cap must be mounted on each of such parts and this again increases the time required in making preparations for a surgical operation. This, both the drape and the sterile cap have encountered considerable difficulty in use.

The sterilization of a microscope for operations is held to be particularly necessary in neurosurgical and orthapedical operations in order to protect the patient, surgeon and other operating staff-members against injections. To meet this requirement, the microscope for operation body and its support arm portions are commonly enclosed with covers made from sterile fabrics or synthetic resins in a bag shape. However, if the sterile cover has loose portions, it may prevent smooth movements of the support arm portions or the loose portions may accidentally contact non-sterile parts, thereby interfering with the surgical operation. To avoid these problems, binding the sterile cover to the support arm portions and the like by fastening means such as tie strings or rubber bands is commonly practiced. However, depending on the binding position or strength, the movable range of the support arm portions may be narrowed, thereby making it impossible for the microscope for operation to be manipulated to the fullest extent. As a further problem, the loosening of the portions of the cover other than those which are bound with strings or rubber bands is not completely eliminated and the portions that remain loose can potentially obstruct the vision of the surgeon. Thus, the manipulability of the microscope for operation has been more or less dependent on the skill of the operating staff-member who binds the cover to the support arm portions and the like by strings or rubber bands.

Another example of the sterile drape is disclosed in U.S. Pat. No. 3,698,791. This is a deformable drape generally adapted to the shape of the microscope for operation such that it can completely cover the latter in one action. A different approach is disclosed in U.S. Pat. No. 5,355,292 and covers that can be sterilized by autoclaving or the like are placed over the respective handles of the microscope for operation to be used and the surgeon will manipulate only the covered handles so as to keep them in a sterile condition throughout the surgical operation.

The drape shown in U.S. Pat. No. 3,698,791 is convenient in that it can cover the whole part of the microscope for operation in one action but on the other hand any unwanted loose portions of the drape have to be secured to selected parts of the microscope because they will reduce the efficiency of surgical operations by interfering with the smooth movements of the surgeon's hands or obstructing his or her vision during observation with the naked eye. However, if the number of sites where loose portions are secured or the amount in which they are secured is increased, smooth movements of the arms for moving the microscope for operation body and other parts that make relative movements to one another may be prevented, thereby rendering it impossible for the microscope to exhibit its intended performance. Needless to say, securing the loose portions of the drape to selected parts of the microscope for operation while check is made to insure that those parts which are to make relative movements move smoothly is a very tedious job. What is more, in order to manipulate the covered parts of the microscope for operation as in making pupil distance adjustments or manual zooming, the parts under manipulation have to be grasped through the drape but slippage often occurs between the microscope and the drape, thereby reducing its manipulability. Another problem with the drape disclosed in U.S. Pat. No. 3,698,791 is that being of a bag shape, it must have a sufficient bore to admit the largest-diameter portion of the microscope for operation and this results in the formation of too many loose portions.

In order to eliminate the loose portions of the bag-shaped drape after it has been mounted over the microscope for operation, U.S. Pat. No. 3,698,791 proposes the use of bands. However, as already mentioned, eliminating the loose portions of the drape in a satisfactory manner for practical purposes is difficult and, what is more, when those parts of the microscope for operation which are adapted to move relative to one another move during the surgical operation, the applied bands may be displaced in such a way as to increase the sag of loose portions. According to U.S. Pat. Nos. 4,045,118 and 4,561,540, tear lines are formed in selected areas of the drape and the unwanted portions of the drape will be severed off along those tear lines after it has been placed over the microscope for operation. A problem with this proposal is that if an excessive force is inadvertently applied to the microscope when the unwanted portions of the drape are cut off, the diopter of the eyepieces might deviate from preset values or they could fail to function properly.

A clinical practice that is gaining popularity today in the field is using an endoscope in order to examine "blind areas" which are inaccessible to a microscope for operation as disclosed in Unexamined Published Japanese Patent Application No. Hei. 6-000196. An endoscope is to be inserted into a body cavity, so it is sterilized separately and independently from the microscope for operation. Hence, according to the patent reference, supra, the drape for a one-piece assembly of an microscope for operation and endoscope combination has a hole through which the tip of the objective lens of the endoscope is to be exposed. However, if the drape is placed over the one-piece combination of a microscope for operation and an endoscope, the endoscope which has been sterilized independently of the drape may be contaminated by the inside surface of the bag-shaped drape which may have been contacted by non-sterile portions of the equipment. As a further problem, the hole through which the tip of the objective lens of the endoscope is to be exposed may also allow the microscope for operation to become exposed, thereby impairing the integrity of sterilization.

Further, as taught in U.S. Pat. No. 3,698,791, the drape is usually delivered in a folded condition to hospitals, where it is unfolded into a bag shape so that it can be placed over the microscope for operation. In order to insure that the inner surface of the bag which will contact the microscope for operation when it is covered by the drape will not be touched by non-sterile personnel, the drape as it is delivered to hospitals is folded in such a way that said inner surface will come outside. In fact, however, the drape is typically made of transparent vinyl polymers, so when it is in a folded condition, it is hard to tell which side is the interior and which is the exterior and this can potentially lead to the contamination of these areas which should be kept in a sterile condition.

The cover described in U.S. Pat. No. 5,355,292 is provided with a cover flange that prevents the surgeon' hand from contacting any non-sterile portions of the handle while he is manipulating it. However, the cover having this flange is not as effective as the drape which enables the surgeon to manipulate the handle without looking away from the eyepieces and the efficiency of the surgical operation will unavoidably decrease since the surgeon has to look away from the eyepieces each time he or she wants to make sure that there is no contact with the non-sterile portions of the equipment.

SUMMARY OF THE INVENTION

The present invention has been accomplished under these circumstances of the prior art and has as a first object providing a sterile instrument for use on a microscope for operations that enables the whole part of the microscope for operation body to be easily rendered in an aseptic condition so that no great time is needed to make preparations for a surgical operation and which also allows a cap or caps to be positively retained on the microscope for operation body.

A second object of the invention is to provide a sterile instrument for use on a microscope for operations that can be brought into intimate contact with any desired portions such as the support arm portions of a microscope for operation and which yet improves the manipulability of the respective moving parts of the microscope without compromising the smoothness of their movements.

These objects of the invention can generally be attained by a sterile instrument that is to be placed over a microscope for operation such as to keep the outer surfaces of the microscope in an aseptic condition, which is characterized by comprising two portions, one having a shape which, when said sterile instrument is placed over the microscope for operation, is substantially adapted to the exterior shape of said microscope for operation and being capable of following the movement of those parts of the microscope which make relative movements to one another and the other being a substantially non-deformable portion that fits to at least part of said microscope.

If a cap is to be mounted over the body of the microscope for operation body so that it can be used in an aseptic condition, the surgeon or an authorized operating staff member opens a sterile cap and places it from above the microscope body. The cap is further advanced until it comes in intimate contact with the shape of said microscope body. If the operating of the cap is closed, the retaining portion of the microscope body makes a snug fit with the mounting hole in the cap, whereupon the entire part of the microscope body is covered with the cap which is positively mounted over the microscope body.

A sterile instrument for use on a microscope for operations according to a second aspect of the invention has a heat-shrinkable material used in at least part of the member. In this case, a sterile instrument shrinking apparatus and the microscope for operation are equipped with means for heating the sterile instrument.

A sterile instrument for use on a microscope for operations according to a third aspect of the invention has a deformable portion provided in those areas which correspond to the parts of the microscope for operation which are capable of variations in its exterior shape during a surgical operation whereas a non-deformable member that can be fixed to the microscope for operation and that has the same exterior shape as the latter is provided in other areas. As in the prior art, the entire part of the microscope for operation is covered with the sterile instrument (drape), with the non-deformable member being fixed to the corresponding parts of the microscope.

A sterile instrument for use on a microscope for operations according to a fourth aspect of the invention has a deformable member provided at the opening of the sterile instrument and the diameter of said opening is variable such that it increases when the sterile instrument is being placed over the microscope but decreases after it has been placed in position.

A sterile instrument for use on a microscope for operations according to a fifth aspect of the invention has said deformable and non-deformable members as separate entities. As in the prior art, the whole part of the microscope for operation is covered with the deformable member alone and thereafter the non-deformable member is secured to the corresponding parts of the microscope via said deformable member.

A sterile instrument for use on a microscope for operations according to a sixth aspect of the invention is characterized in that said non-deformable member has means for accommodating or breaking said deformable member. When the non-deformable member is secured to the microscope for operation via said deformable member, part of the deformable member is accommodated by or broken by the non-deformable member.

A sterile instrument for use on a microscope for operations according to a seventh aspect of the invention is characterized in that said non-deformable member has means for retaining a surgical instrument that has been sterilized by a different method than has been used to provide said sterile instrument. After the non-deformable member is secured to the corresponding parts of the microscope for operation, a surgical instrument that has been sterilized by a different method is retained by the non-deformable member.

A sterile instrument for use on a microscope for operations according to an eighth aspect of the invention is characterized in that the deformable portion has a simple tubular form and is to be received by an annular accommodating portion consisting of a plurality of cross sections that profile the corresponding cross sections of the tube. When the annular accommodating portion is passed over the microscope for operation, the deformable member will come telescopically out of said annular accommodating portion until it covers the microscope for operation.

A sterile instrument for use on a microscope for operations according to a ninth aspect of the invention has means for eliminating the projection of any manipulation knob on an microscope for operation that will interfere with the securing of the non-deformable member to the microscope for operation. By using said means, the projection of any undesirable manipulation knob is eliminated before the nondeformable member is secured to the microscope for operation.

A sterile instrument for use on a microscope for operations according to a tenth aspect of the invention is characterized in that the means for eliminating the projection of any undesirable manipulation knob on a microscope for operation is a mechanism for mounting or dismounting said manipulation knob. Any undesirable manipulation knob is detached from the microscope for operation before the nondeformable member is secured to it.

A sterile instrument for use on a microscope for operations according to an eleventh aspect of the invention is characterized in that the means for eliminating the projection of any undesirable manipulation knob on a microscope for operation is a mechanism for advancing or retracting said manipulation knob. Any undesirable manipulation knob is pushed into the microscope for operation before the non-deformable member is secured to it.

BRIEF DESCRIPTION OF THE DRAWINGS

FIG. 7 shows the retaining and mounting portions in the first embodiment as they have been brought into engagement with each other;

FIG. 8 is a perspective view of a microscope for operation body for use in a second embodiment of the invention;

FIG. 9 is a perspective view of a sterile cap according to the second embodiment;

FIG. 10 is a side view showing in longitudinal section the relative positions of a diopter adjusting ring and a diopter adjusting cap in the second embodiment;

FIG. 11 is side view showing in longitudinal section the relative portions of a pupil distance adjusting knob and a pupil distance adjusting cap in the second embodiment;

FIG. 12 is a section showing a modification of the second embodiment;

FIG. 13 is a perspective view of a microscope for operation body or use in a third embodiment of the invention;

FIG. 14 is a perspective view of a sterile cap according to the third embodiment;

FIG. 23 is a perspective view showing part of the sterile drape of the fifth embodiment which is fitted with a fastener;

FIG. 24 is a perspective view of a sterile drape according to a sixth embodiment of the invention;

FIG. 25 is a perspective view showing sterile caps according to the sixth embodiment;

FIG. 26 is a side view showing in longitudinal section one of the sterile caps according to the sixth embodiment;

FIG. 27 is a side view showing in longitudinal section another sterile cap according to the sixth embodiment;

FIG. 28 is a perspective view showing a microscope for operation body and an ocular lens barrel for use in the sixth embodiment;

FIG. 29 is a side view showing in longitudinal section an eyepiece for use in the sixth embodiment;

FIG. 30 is a perspective view showing the sterile drape as it has been placed over the microscope for operation in the sixth embodiment,;

FIG. 51 shows the general layout of a thirteenth embodiment of the invention;

FIG. 52 shows in detail the structure of the heat generating unit in the thirteenth embodiment; and FIG. 53 shows the general layout of a fourteenth embodiment of the invention.

DETAILED DESCRIPTION OF THE INVENTION

Various embodiments of the invention will now be described with reference to the accompanying drawings.

Figure 1:
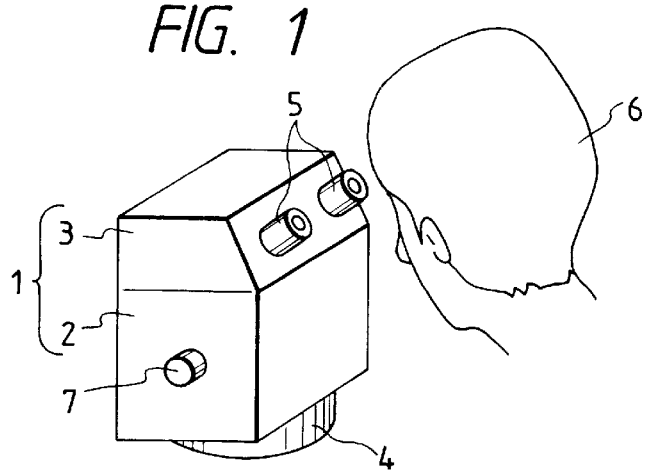
FIG. 1 is a perspective view of a microscope for operation body for use in a first embodiment of the invention.

FIGS. 1–7 show a first embodiment of the invention. FIG. 1 shows the exterior appearance of a microscope for operation for use in the first embodiment. Reference numeral 1 refers to a microscope for operation body mounted on arms (not shown) capable of three-dimensional movements to be fixed in a desired position; the microscope body 1 consists of a main body portion 2 and a lens mount 3. An objective lens 4 is provided on the underside of the main body 2 and eye-pieces 5 are provided on an inclined side of the lens mount 3. Generally cylindrical retaining portions 7 are provided to project from both the right and left sides of the main body portion 2 as seen from the surgeon 6.

Figure 2:
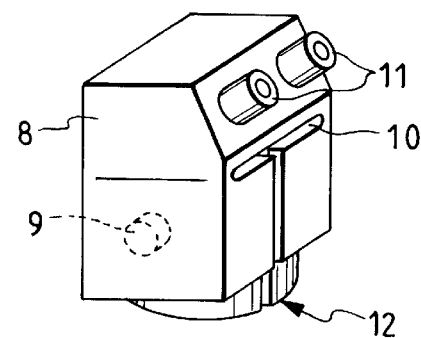
FIG. 2 is a perspective view of a sterile cap according to the first embodiment.

FIG. 2 shows the exterior appearance of a cap 8 that can be mounted over the microscope for operation body 1 and it is formed of an elastic or resilient material such as rubber that can be sterilized by autoclaving. The interior of the cap 8 has substantially the same shape as the microscope body 1 and is of a sufficient size to cover it completely. Provided on the inner surfaces of both the right and left sides of the cap 8 are mounting portions 9 that are of such a size and in such a position that the cap 8 can be fixed by the retaining portions 7 when it is mounted over the microscope body 1.

The cap 8 also has an opening 10 on the front side that permits the cap 8 to be opened to such an extent that it can be easily mounted over the microscope body 1 when required. The opening 10 has on its entire periphery a flange (not shown) that permits the opening 10 to be sufficiently closed so that the microscope body 1 will not be exposed when the cap 8 has been mounted over it.

Eyepiece cover portions 11 that can be fitted over the eyepieces 5 are provided in the upper part of the cap 8, and an objective window 12 is provided on the underside of the cap 8 in such a way that the rays of light passing through the objective lens 4 will not be blocked when the cap 8 is mounted over the microscope body 1.

The structures of the retaining portion 7 and the mounting portion 9 will now be described with reference to FIGS. 3 and 4.

Figure 3:
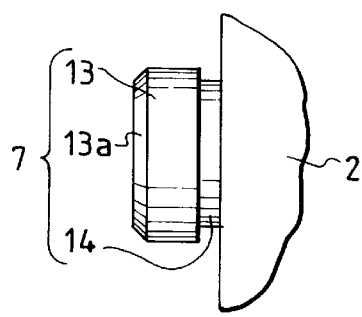
FIG. 3 is a side view of a retaining portion provided on the microscope operating body in the first embodiment.

FIG. 3 shows the overall structure of the retaining portion 7. Shown by 13 is a cylindrical projection that is chamfered at the distal end 13a to permit easy insertion into the mounting portion 9. The projection 13 also has an annular groove 14 formed around the base.

Figure 4:
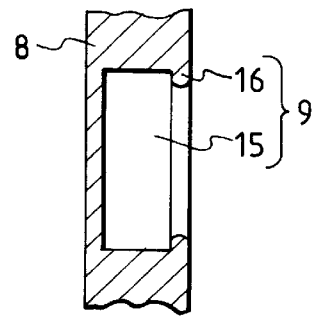
FIG. 4 is a side view showing in longitudinal section a mounting portion provided on the cap according to the first embodiment.

FIG. 4 shows the overall structure of the mounting portion 9. A mounting hole 15 has an interior shape which is generally the same as the exterior shape of the projection 13 and which is of such a size that the projection 13 can be inserted and fitted into the mounting portion 9. The mounting hole 15 has an annular rib 16 formed at the open end to encircle the vicinity of its entrance. The inside diameter of the annular rib 16 is smaller than the outside diameter of the projection 13 and the width of the annular rib 16 is smaller than that of the annular groove 14 so that the annular rib 16 can be fitted into the annular groove 14.

Figure 5:
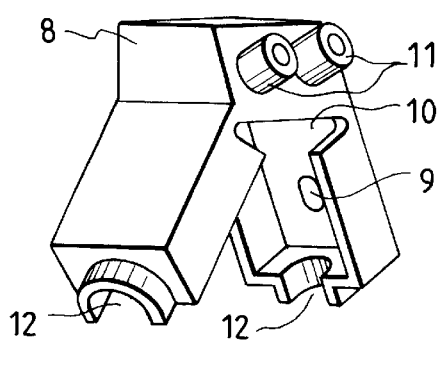
FIG. 5 is a perspective view showing the cap of the first embodiment as it has been opened wide enough to be placed over a microscope for operation.
Figure 6:
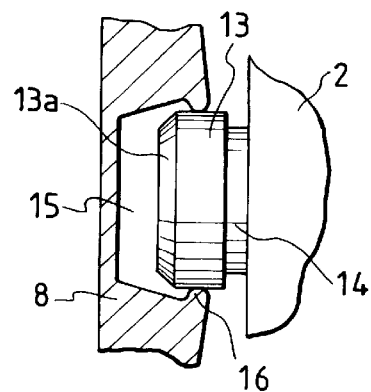
FIG. 6 shows how the retaining and mounting portions in the first embodiment are being brought into engagement with each other.

The operations of the thus constructed body 1 and the cap 8 will now be described. First consider the case where the cap 8 is mounted over the microscope for operation body 1 to use it in a sterile condition. As shown in FIG. 5, the surgeon 6 (see FIG. 8) or any authorized operating staff member holds the sterile cap 8 and renders the opening 10 sufficiently wide so that the cap 8 can be slipped over the lens mount 3 from above. Then, deform the cap 8 and insert the eyepieces 5 into the eyepiece lens cover portions 11 until they are brought into a snug-fit relationship.

Thereafter, close the opening 10 while making sure that the cap 8 contacts intimately with the outer shapes of the lens mount 3 and the main body portion 2. In the next step, deform the mounting portion 9 on the cap 8 so that the projection 13 is inserted into the mounting hole 15 (see FIG. 6), whereupon the projecting part 13 of the retaining portion 7 on the microscope body 1 is fitted into the mounting hole 15 in the cap 8. Since the annular rib 16 is also fitted into the annular groove 14, the entire part of the microscope body 1 is covered with the cap 8, which is positively mounted over the body 1.

The first embodiment described above can be realized by a simple construction in which the retaining portion 7 which enables the cap 8 to be mounted over the microscope-body 1 is provided on the main body portion 2 of the microscope body 1. The conventional sterilizable cap is of such a type that it is only mounted over the manipulable parts of the microscope for operation body and it has been difficult to render the whole part of the microscope body in a sterile condition by the sole use of the cap. In addition, a plurality of caps have to be used to attain the same result as covering the whole part of the microscope. In contrast, the sterilizable cap 8 according to the first embodiment is capable of covering the whole part of the microscope for operation body 1 and it is not only provided with the opening 10 but also formed of an elastic material such as rubber so that the opening 10 can be made wide enough to permit very smooth mounting of the cap 8 over the body 1. As a further advantage, the cap 8 is formed as a one-piece construction, so it is simple to handle and can be mounted over the microscope for operation body 1 without taking an unduly long time in making preparations for a surgical operation.

In the first embodiment described above, the main body portion 2 and the cap 8 are provided with the retaining portion 7 and the mounting portion 9, respectively, as means for fixing them to each other; needless to say, the same result is attained by providing the main body portion 2 and the cap 8 with magnetic elements of opposite polarities.

FIGS. 8—12 show a second embodiment of the invention and the parts or components that are identical to those used in the first embodiment are identified by like numerals and will not be described again.

FIG. 8 shows the overall structure of a microscope for operation for use in the second embodiment. An eyepiece unit 5 has a lens barrel 17 fitted with a diopter adjusting ring 18. By rotating the ring 18 relative to the lens barrel 17 about the viewing optical axis $O_1$ of the eyepiece unit 5, part of the lens elements in the eyepiece unit 5 can be moved along the optical axis $O_1$, thereby adjusting the diopter.

The microscope for operation body 1 has an inclined lens mount 19 on the main body portion 2 which has the eyepiece unit 5 and which is capable of varying its angle with respect to the main body portion 2 in directions indicated by double-headed arrow a. A pupil distance adjusting knob 20 of a well-known mechanism which corresponds to the retaining portion of the invention is provided on both the right and left sides of the lens mount 19 as seen from the surgeon 6. The pupil distance adjusting knob 20 is a cylinder that can be rotated about central axis $O_2$ to vary the distance between the two eyepieces 5.

A zooming knob 21 which also corresponds to the retaining portion of the invention is provided on both the right and left sides of the main body portion 2 and when it is rotated about axis $O_3$, the zoom lens unit (not shown) contained in the main body portion 2 is moved to vary the viewing magnification. The zooming knob 21 is also a cylinder that can be rotated about the central axis $O_3$. The pupil distance adjusting knob 20 and the zooming knob 21 are each provided with a V-shaped groove 22 that surrounds their entire circumference (see FIG. 11).

A cap that can be mounted over the microscope for operation body 1, namely, the combination of the main body portion 2 and the inclined lens mount 19, will now be described with reference to FIG. 9. The cap generally indicated by 23 is formed primarily of a hard or rigid material that can be sterilized by autoclaving and partly of an elastic material such as rubber that can also be sterilized by autoclaving, and it consists of a left cap 23a and a right cap 23b. The right cap 23b has mounting pins 24, and the left cap 23a has pin receptacles 25 that are provided in such positions that, when the cap 23 is mounted over the microscope for operation body 1, those receptacles 25 come into engagement with the mounting pins 24; hence, the cap 23 can be fabricated as a unitary assembly by fitting the mounting pins 24 into the corresponding pin receptacles 25.

A flexible bellows 26 that is made of an elastic material such as rubber is provided in that area of the cap 23 which, when it is mounted over the microscope for operation body 1, corresponds to the moving parts of the main body portion 2 and the inclined lens mount 19. In addition, a pupil distance adjusting cap 27 and a zooming cap 28 are provided on both the right and left sides of the cap 23 as seen from the surgeon 6; the caps 27 are made of a hard material and can be fitted over the pupil distance adjusting knobs 20 provided on the lens mount 19, and the zooming caps 28 are also made of a hard material and can be fitted over the zooming knobs 21.

The eyepiece cover portions 11 will now be described with reference to FIG. 10. Shown by 29 is a diopter adjusting cap, which is formed to have such an interior shape that its inner circumference is shorter than the outer circumference of the diopter adjusting ring 18 to achieve snug fit over the latter, and the adjusting cap 29 has a flange 30 formed around its outer circumference.

The diopter adjusting cap 29 is provided with an ocular window 31 through which the eyepiece 5 can be observed. The adjusting cap 29 is also provided with a bellows 32 that is made of an elastic material such as rubber and which is deformable in two directions, one being parallel and the other normal to the paper. A flange receptacle 33 for retaining the flange 30 is provided in order to prevent the diopter adjusting cap 29 from slipping out of the diopter adjusting ring 18. The flange receptacle 33 retains the diopter adjusting cap 29 in such a way that it is capable of rotation about the viewing optical axis $O_1$ of the eyepiece 5.

The pupil distance adjusting cap 27 and the zooming cap 28 will now be described more specifically with reference to FIG. 11. Since both caps have the same structure, the following description is directed only to the pupil distance adjusting cap 27. A flange 34 is provided around the outer circumference of the cap 27. Bonded to the inner circumference of the cap 27 is an O-ring 35 that is made of an elastic material such as rubber and that can be fitted into the V-shaped groove 22 provided in the pupil distance adjusting knob 20. The inner circumference of the O-ring 35 is smaller than the outer circumference of the knob 20. The pupil distance adjusting cap 27 has a flange receptacle 36 that retains the flange 34 and which prevents the cap 27 from slipping out of the knob 20 by retaining it in such a way that it is capable of rotating about the central axis $O_2$ of the knob 20.

The operations of the thus constructed microscope for operation body 1 and cap 23 will now be described. Consider first the case of using the microscope for operation body 1 as it is covered with the cap 23. The surgeon 6 or any authorized operating staff member disassembles the cap 23 into the left cap 23a and the right cap 23b and sterilize them individually. Then, the bellows 32 of the eyepiece cover portion 11 of either cap, say, the left cap 23a, is deformed such that said cap is slipped over the inclined lens mount 19 from above as seen from the surgeon 6 until the diopter adjusting ring 18 on the eyepiece 5 is fitted into the diopter adjusting cap 29 of the eyepiece cover portion 11.

The bellows 32 are further deformed such that the pupil distance adjusting cap 27 is fitted over the pupil distance adjusting knob 20 provided on the left side of the inclined lens mount 19 as seen from the surgeon 6 until the O-ring 35 bonded to the cap 27 is fitted into the V-shaped groove 22 in the knob 20. Similarly, the zooming cap 28 is fitted over the zooming knob 21 provided on the left side of the main body portion 2 as seen from the surgeon 6 until the O-ring 35 is fitted into the corresponding V-shaped groove 22. Thus, the microscope for operation body 1 is made integral with the left cap 23a when the V-shaped grooves 22 provided in the pupil distance adjusting knob 20 and the zooming knob have been brought into snug-fit engagement with the O-rings 35 provided on the pupil distance adjusting cap 27 and the zooming cap 28. The same procedure may be employed to make the right cap 23b integral with the microscope for operation body 1 by mounting it over the main body portion 2 and the inclined lens mount 19. Thereafter, the mounting pins 24 provided on the right cap 23b are fitted into the pin receptacles 25 provided on the left cap 23a, whereby the left cap 23a and the right cap 23a can be combined into a unitary assembly in such a way that the microscope for operation 1 is entirely covered with the cap-23 to leave no part exposed.

The surgeon 6 then makes the following preparations for his surgical operation. To make a diopter adjustment, he causes each of the diopter adjusting caps 29 on the eyepiece cover portion 11 to rotate around the viewing optical axis $O_1$ with respect to the cap 23, whereupon the diopter adjusting ring 18 fitted into each cap 29 moves together with the latter relative to the lens barrel 17 so as to adjust the diopter of the eyepiece unit 5 to the value the surgeon 6 desires. At the same time, the diopter adjusting rings 18 are moved along the viewing optical axis $O_1$ relative to the lens barrel 17, thereby causing a deformation of the bellows 32 provided on the eyepiece cover portion 11.

If the surgeon 6 wants to adjust the pupil distance, he may rotate each of the pupil distance adjusting caps 27 around the axis $O_2$ relative to the cap 23, whereupon the pupil distance adjusting knob 20 fitted into each pupil distance adjusting cap 27 rotates together with the latter relative to the inclined lens mount 19 so as to adjust the distance between the two eyepieces 5 to the value the surgeon 6 desires.

In response to the movement of the eyepieces 5 with respect to the inclined lens mount 19, the diopter adjusting cap 29 which are fitted over the diopter adjusting rings 18 on the eyepiece unit 5 are moved in the same direction as the eyepieces 5 are moved. As a result, the flange receptacles 33 holding the diopter adjusting caps 29 will move together with the latter to cause a deformation of the bellows 32.

If the surgeon 6 while performing the surgical operation wants to incline the lens mount 19 in directions of a so that it forms a desired angle with the main body portion 2, he may first grasp the lens mount 19 through the cap 23 and inclines it in the desired direction so that the bellows 26 provided on the cap 23 will deform together with the moving parts of the main body portion 2 and the lens mount 19. If the surgeon 6 wants to change the viewing magnification to a desired value, he may rotate each of the zooming caps 28 around the axis $O_3$ relative to the cap 23, whereupon the zooming knobs 21 which are in snug-fit engagement with the zooming caps 28 by means of V-shaped grooves 22 and a-rings 35, will rotate relative to the main body portion 2 together with the rotating zooming caps 28.

According to the second embodiment described above, manipulation knobs such as the pupil distance adjusting knobs or zooming knobs that are usually provided on the microscope for operations are also used as means for assisting in the mounting of a sterilizable cap over the microscope for operation and this eliminates the need to provide a special structural element for assisting in the mounting of a sterilizable cap.

No such moving parts have been provided for the conventional caps that can be sterilized by autoclaving, so if one wants to mount the cap over a microscope for operation body having moving parts, the only way he can adopt is to provide a cap for each of the moving parts or to mount caps exclusively over the manipulating parts which the surgeon actually touches by hand for manipulation during the surgical operation. In the second embodiment of the invention, the cap 23 that is sterilizable and which is large enough to cover the entire part of the microscope for operation body 1 is provided with bellows 26 and 32 which are made of a deformable elastic material such as rubber and, in addition, caps are provided in such a way that they can be fitted over and can move together with the diopter adjusting rings 18, pupil distance adjusting knobs 20 and zooming knobs 21 which are provided on the microscope body 1; as a result, the microscope for operation body 1 having movable parts can be manipulated as desired and yet with the whole part of it being kept in an aseptic condition. In addition, the cap 23 is splittable into two parts, the left cap 23a and the right cap 23b, and all parts of the cap 23 except the moving parts are made of a hard material; therefore, the cap 23 has such a good self-supporting property that it can be mounted over the microscope for operation body 1 very efficiently to insure that the entire part of it is covered with the cap 23 leaving no part exposed.

In the foregoing description, mounting pins 24 and pin receptacles 25 are used as means for connecting the left cap 23a and the right cap 23b into a unitary assembly. Needless to say, the same result can be attained by using magnetic elements having opposite polarities or, alternatively, by providing mutually engageable hooks 36 on both the left and right caps 23a and 23b as shown in FIG. 12.

FIGS. 13 and 14 show a third embodiment of the invention and the parts or components that are identical to those used in the first and second embodiments are identified by like numerals and will not be described again.

FIG. 13 shows the overall structure of a microscope for operation for use in the third embodiment. A first electromagnetic coil 37 that corresponds to the retaining portion of the invention and which is capable of producing a magnetic field outside the inclined lens mount 19 is provided in its interior on both the right and left sides as seen from the surgeon 6. A second electromagnetic coil 38 which also corresponds to the retaining portion of the invention and which is capable of producing a magnetic field outside the main body portion 2 is provided in its interior on both the right and left sides as seen from the surgeon 6.

The main body portion 2 has on its underside a frame 39 for the objective lens (not shown). The first electromagnetic coil 37 and the second electromagnetic coil 38 are so designed that the surgeon 6 or any authorized operating staff member can selectively produce a magnetic field by turning on or off a switch (not shown) or some other suitable means.

We now explain a cap 40 that consists of an upper cap 40a and a lower cap 40b and that can be mounted over the microscope for operation body 1 which consists of the main body portion 2 and the inclined lens mount 19. The upper cap 40a is primarily formed of a hard material that can be sterilized by autoclaving and partly of an elastic material such as rubber that can also be sterilized by autoclaving. The underside of the upper cap 40a is provided with an opening 41 large enough to insure that it can be smoothly mounted over the inclined lens mount 19, and the interior shape of the upper cap 40a is generally the same as the exterior shape of the inclined lens mount 19.

A bellows 42 that is made of an elastic material such as rubber is provided in that area of the upper cap 40a which, when it is mounted over the inclined lens mount 19, corresponds to the moving parts of the main body portion 2 and the inclined lens mount 19. In addition, a first attractable portion 43 that is made of a metallic material and that can be attracted to the inclined lens mount 19 by magnetism is provided in the interior of the upper cap 40a in such a position that the magnetic field produced by the first electromagnetic coil 37 can be picked up when the upper cap 40a has been mounted over the inclined lens mount 19.

The lower cap 40b is formed of a hard material that can be sterilized by autoclaving. The top of the lower cap 40b is provided with an opening 44 large enough to insure that it can be smoothly fitted over the main body portion 2 and the interior shape of the lower cap 40b is generally the same as the exterior shape of the main body portion 2.

A second attractable portion 45 that is made of a metallic material and that can be attracted to the main body portion 2 by magnetism is provided in the interior of the lower cap 40b in such a position that the magnetic field produced by the second electromagnetic coil 38 can be picked up when the lower cap 40b has been mounted over the main body portion 2. The underside of the lower cap 40b is provided with an objective lens cover portion 46 of such a shape and size that it can be fitted over the objective lens frame 39 provided on the main body portion 2.

The magnetic field produced by the first and second electromagnetic coils 37 and 38 and the attraction it provides between the microscope for operation body 1 and each of the upper and lower caps 40a and 40b are of such magnitudes that the upper and lower caps 40a and 40b are sufficiently attracted to the body 1 so that they will not drop even if the main body portion 2 and the lens mount 19 are inclined at any angles. In addition, the bellows 42 of the upper cap 40a is of such a length that it can cover part of the lower cap 40b.

We now describe the operations of the thus constructed microscope for operation body 1 and upper and lower caps 40a and 40b. First consider the case where the upper and lower caps 40a and 40b which can be sterilized are mounted over the microscope for operation body 1 which consists of the main body portion 2 and the inclined lens mount 19 so that said body 1 is used in a sterile condition. The surgeon 6 or an authorized operating staff member manipulates a switch (not shown) or some other suitable means such as to cut off the production of a magnetic field from the first and second electromagnetic coils 37 and 38. Then, the sterile supper cap 40a, with the opening 41 facing down, is slipped over the lens mount 19 from above as seen from the surgeon 6 such that the eyepieces 5 are fitted into the eyepiece cover portions 11.

Then, the surgeon 6 manipulates the switch or some other suitable means to produce a magnetic field from the first magnetic coils 37, whereupon the first attractable portions 43 are attracted to the lens mount 19 by the magnetism produced from the first electromagnetic coils 37 so that the upper cap 40a is made integral with the lens mount 19.

To mount the lower cap 40b over the main body portion 2, the sterile lower cap 40b, with the opening 44 facing up, is slipped over the main body portion 2 from below as seen from the surgeon 6 such that the objective lens frame 39 is fitted into the objective lens cover portion 46. In the next step, the surgeon 6 or an authorized operating staff member manipulates the switch or the like such as to produce a magnetic field from the second electromagnetic coils 38, whereupon the second attractable portions 45 are attracted to the main body portion 2 by the magnetism produced from the second electromagnetic coils 38 so that the lower cap 40b is made integral with the main body portion 2.

If the surgeon 6 while performing the surgical operation wants to incline the lens mount 19 so that it forms a desired angle with the main body portion 2, he may first grasp the lens mount 19 through the upper cap 40a and inclines it to the desired position so that the bellows 42 provided on the upper cap 40a which is made of an elastic material such as rubber will deform accordingly.

In order to dismount the upper and lower caps 40a and 40b from the microscope for operation body 1 after the surgical operation ends, the surgeon 6 or an authorized operating staff member may manipulate the switch (not shown) or some other suitable means such as to cut off the magnetic field being produced from the first and second electromagnetic coils 37 and 38, whereupon the first and second attractable portions 43 and 45 are no longer attracted to the lens mount 19 and he main body portion 2, respectively.

According to the third embodiment described above, the first and second electromagnetic coils 37 and 38 are provided within the main body portion 2 and the inclined lens mount 19, respectively, and the surgeon 6 or any authorized operating staff member may simply manipulate a switch or some other suitable mans such as to perform on-off control over the magnetic field produced by those electromagnetic coils; thus, the sterilizable upper and lower caps 40a and 40b can be easily mounted over or dismounted from the main body portion 2 and the lens mount 19, respectively.

As a further advantage, the attraction by the magnetic forces produced from the first and second electromagnetic coils 37 and 38 can positively retain the upper and lower caps 40a and 40b. What is more, no means for helping the upper and lower caps 40a and 40b be mounted over the main body portion 2 and the lens mount 19, respectively, need be provided on the outer surfaces of these parts and, hence, their exterior appearance can be simplified to permit effective cleaning.

In addition, the cap 40 which is large enough to cover the entire part of the sterilizable microscope for operation 1 is fabricated as a simple two-piece construction consisting of the upper and lower caps 40a and 40b and the bellows 42 made of an elastic material such as rubber is provided only in the upper cap 40a. This not only permits easy and economic fabrication of the cap 40 but also ensures that it can be easily mounted over or dismounted from the microscope for operation body 1. When the cap 40 has been mounted over the microscope for operation body 1, the parting line between the upper and lower caps 40a and 40b is covered with the bellows 42 made of an elastic material such as rubber which is provided on the upper cap 40a and this eliminates the possibility that the main body portion 2 or the lens mount 19 will become exposed along the parting line.

In the foregoing description, the first and second electromagnetic coils 37 and 38 are employed to have the cap 40 attracted to the microscope for operation body 1 but they may be replaced by permanent magnets for realizing better cost effectiveness.

Figure 15:
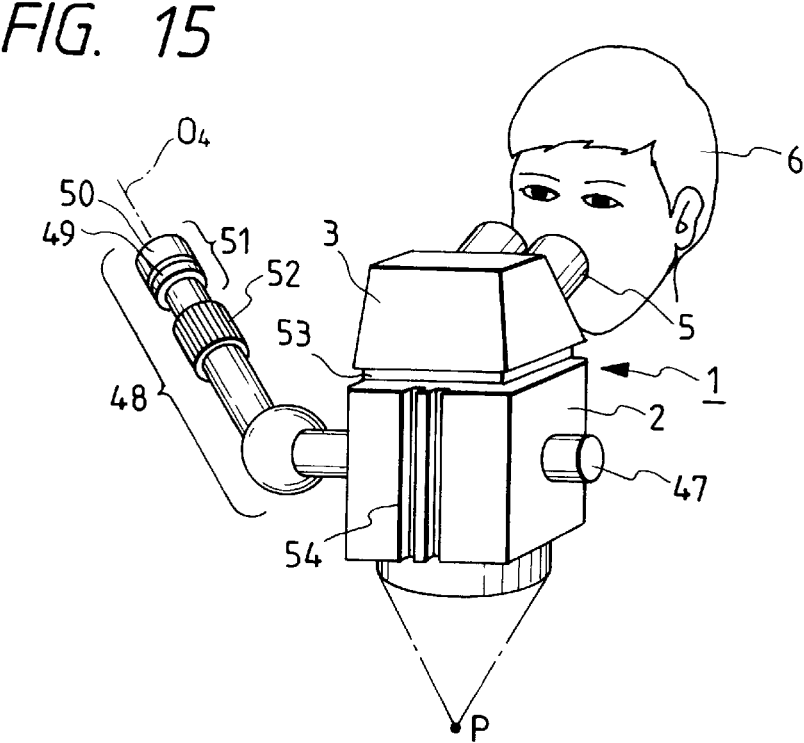
FIG. 15 is a perspective view of a microscope for operation body for use in a fourth embodiment of the invention.
Figure 16:
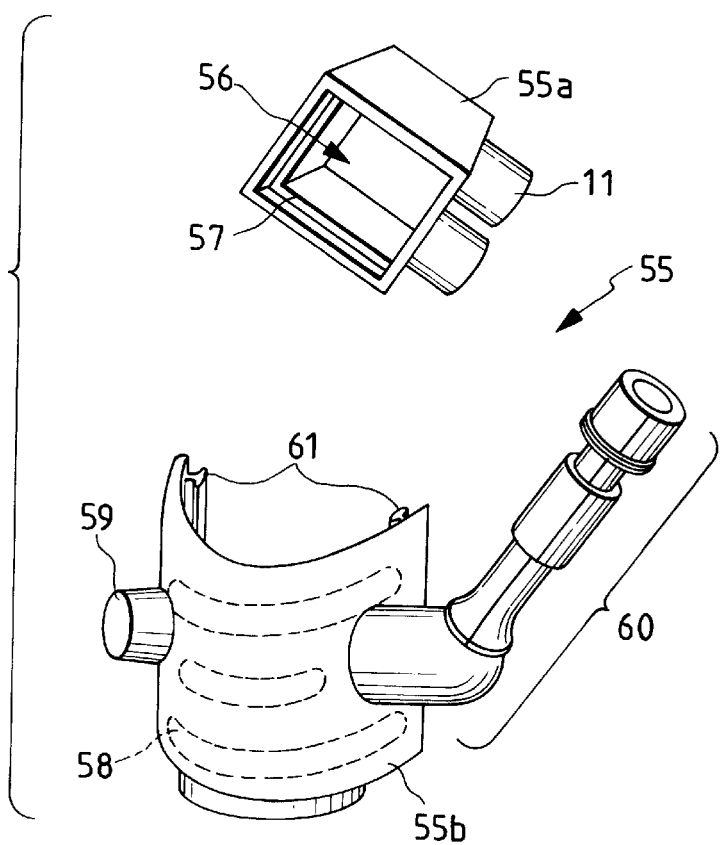
FIG. 16 is a perspective view of a sterile cap according to fourth embodiment.

FIGS. 15–20 show a fourth embodiment of the invention and the parts or components that are identical to those used in the first, second and third embodiments are identified by like numerals. FIG. 15 shows the overall structure of a microscope for operation for use in the fourth embodiment. The microscope for operation body generally indicated by 1 has an adapter portion 47 provided on both the right and left sides of the main body portion 2 as seen from the surgeon 6. The adapter portions 47 are capable of splitting a light beam from a viewing focus P into two beamlets, one of which is guided through a viewing optical path toward an eyepiece 51 and, hence, it can be fitted with an auxiliary viewing device for exclusive use by an assistant or other staff member. In the illustrated case, one of the adapters 47 is detachably provided with a well-known device 48 for examination by an assistant.

The device 48 for examination by an assistant has an eyepiece barrel 49 which in turn is fitted with a diopter adjusting ring 50. The ring 50 may be rotated about the axis $O_2$ with respect to the eyepiece barrel 49, thereby making a diopter adjustment. The eyepiece barrel 49 also contains an eyepiece 51 having the axis $O_4$ as the viewing optical axis, as well as a well-known image rotator mechanism (not shown) with which a viewing image from the eyepiece 51 can be rotated about the axis $O_4$ with respect to the viewing surface of the eyepiece 51. The image rotator mechanism can be driven by rotating a rotator ring 52 about the axis $O_4$ with respect to the device 48 for examination by an assistant.

Shown by 53 is a mounting groove that is provided around the lens mount 3 and which corresponds to the retaining portion of the invention. Shown by 54 are two vertical mounting grooves that are provided on the other side of the main body portion 2 remote from the surgeon 6 and that also correspond to the retaining portion of the invention.

We now explain a cap 55 that consists of an upper cap 55*a* and a lower cap 55*b* and that can be mounted over the microscope for operation body 1 which consists of the main body portion 2 and the lens mount 3. The upper cap 55*a* is formed of an elastic material such as rubber that can be sterilized by autoclaving. The underside of the upper cap 55*a* is provided with an opening 56 large enough to insure that it can be smoothly mounted over the lens mount 3 and the interior shape of the upper cap 55*a* is generally the same as the exterior shape of the lens mount 3.

The upper cap 55*a* also has a projecting portion 57 provided near the opening 56 that can be fitted into the mounting groove 53 provided around the lens mount 3. Like the upper cap 55*a*, the lower cap 55*b* is also formed of an elastic material such as rubber that can be sterilized by autoclaving. The lower cap 55*b* has a plurality of metal sheets 58 inserted therein; being made of a flexible metal, the sheets 58 are free to deform together with the lower cap 55*b*.

The lower cap 55*b* is large enough to cover the entire circumference of the main body portion 2. The lower cap 55*b* is also provided with an accommodating portion 59 having an internal space large enough to receive the adapter portion 47, as well as a cover portion 60 which can be mounted over the device 48 for examination by an assistant.

The lower cap 55*b* is provided with two projections 61 that extend from the side opposite to the directions in which the accommodating portion 59 and the cover portion 60 project. The two projections 61 can be mounted into the grooves 54 provided on the main body portion 2.

Figure 17:
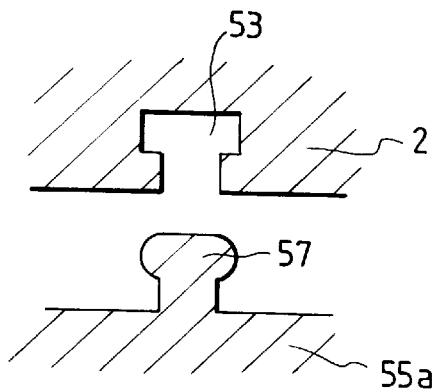
FIG. 17 is a section showing the respective shapes of the engaging portions of the microscope body and the cap in the fourth embodiment.

We now describe the mounting grooves 53 and 54, as well as projections 57 and 61. The mounting groove 53 and the projecting portion 57 have the same structures for mounting as the mounting grooves 54 and the projections 61, respectively, so the following description is directed only to the mounting groove 53 and the projecting portion 57. FIG. 17 shows cross-sectional shapes of the mounting groove 53 and the projecting portion 57. As shown, the mounting groove 53 has such a cross-sectional shape that it is constant in width to a certain depth, beyond which it becomes wider and remains so down to the bottom, whereas the projecting portion 57 has such a cross-sectional shape that it is constant in width to a certain height, beyond which it becomes wider and remains so up to the top. The projecting portion 57 is generally of an identical shape to the mounting groove 53. This is also true with their relative dimensions and the projecting portion 57 is of generally an identical size to the mounting groove 53.

Figure 18:
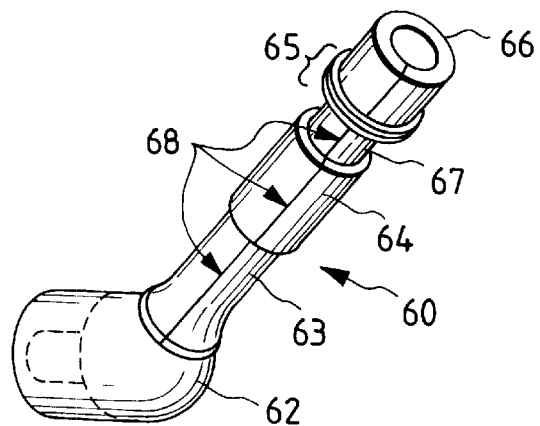
FIG. 18 is a perspective view of the cover portion of the cap according to the fourth embodiment.
Figure 19:
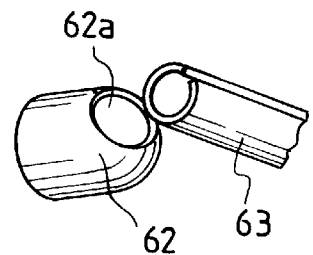
FIG. 19 is a perspective view showing part of the cover portion in the fourth embodiment.

The cover portion 60 which can be mounted over the device 48 for examination by an assistant will now be described in detail with reference to FIG. 18. The cover portion 60 has a basal portion 62 that is formed as an integral part and which has an internal shape and size that permit the cover portion 60 to be smoothly mounted over the device 48 for examination by an assistant. The basal portion 62 has a first cover portion 63 as an integral part that can be bent with respect to the basal portion 62 as shown in FIG. 19. The first cover portion 63 has a leaf spring (not shown) inserted therein.

The basal portion 62 has a mounting hole 62*a* through which part of the device 48 for examination by an assistant can be passed. If the first cover portion 63 is not bent with respect to the basal portion 62, the mounting hole 62*a* will be completely closed by the first cover portion 63 to leave no part exposed to the outside. The first cover portion 63 has a second cover portion 64 provided rotatably at the distal end and a leaf spring is also inserted in this second cover portion 64.

Provided at the distal end of the second cover portion 64 is a third cover portion 67 having a flexible bellows 65 and an eyepiece cover portion 66. A leaf spring is also inserted in this third cover portion 67. The interior shape of the eyepiece cover portion 66 is substantially identical to the exterior shape of the eyepiece 51 and its inner circumference is smaller than the outer circumference of the diopter adjusting ring 50 so that it can be snugly fitted over the latter.

The first, second and third cover portions 63, 64 and 67 each have a flit 68 that runs parallel to their axis of rotation. The slits 68 are each provided with a flange portion (not shown) that insures closing of the slits so that the device 48 for examination by an assistant will not become exposed when it is mounted within those cover portions.

Figure 20:
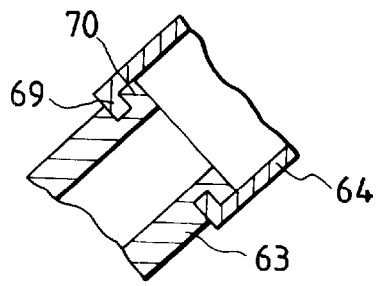
FIG. 20 is a partial section of the cover portion in the fourth embodiment.

The rotating part that connects between the first and second cover portions 63 and 64 and that connects between the second and third cover portions 64 and 67 will now be described with reference to FIG. 20. The part that connects between the first and second cover portions 63 and 64 has the same construction as the part that connects between the second and third cover portions 64 and 67, so the following description is directed only to the part connecting between the first and second cover portions 63 and 64.

The second cover portion 64 has an inward flange 69 at an end and the first cover portion 63 has a flange receptacle 70 at an end that holds the inward flange 69 in a rotatable manner. Thus, the first cover portion 63 and the second cover portion 64 are in rotatable engagement with each other by means of the inward flange 69 and the flange receptacle 70.

We now describe the procedure of mounting the cap 55 over the microscope for operation body 1.

First consider the case where the sterilizable upper cap 55*a* and lower cap 55*b* are mounted over the microscope for operation body 1 consisting of the main body portion 2 and the lens mount 3 such that the surgeon 6 can use the microscope for operation body 1 in a sterile condition. The surgeon 6 or an authorized operating staff member mounts the sterile upper cap 55*a*, with the opening 56 facing down, over the lens mount 3 from above as seen from the surgeon 6 and deforms the upper cap 55*a* made of an elastic material such as rubber in such a way that the eyepiece cover portions 11 are fitted over the eyepieces 5.

The surgeon 6 deforms the projecting part 57 to be fitted into the mounting groove 53 so that the upper cap 55*a* forms an integral assembly with the lens mount 3. The surgeon 6 then mounts the sterile lower cap 55*b* over the main body portion 2; to this end, the device 48 for examination by an assistant which is grasped at the eyepiece 51 is inserted through the mounting hole 62*a* into the basal portion 62 provided on the lower cap 55*b*. In this case, the first cover portion 63 is bent with respect to the basal portion 62.

Then, the slits provided on the first, second and third cover portions 63, 64 and 67, as well as the leaf springs also provided in these cover portions are deformed to open the slits sufficiently wide so that those cover portions can be mounted over the device 48 for examination by an assistant. With the bellows 65 being deformed, the eyepiece cover portion 66 provided on the third cover portion 67 is fitted over the diopter adjusting ring 50 of the eyepiece 51. In the next step, one of the projections 61 provided one the lower cap 55*b* is deformed to be fitted into the corresponding mounting groove 54 on the main body portion 2.

Further, the metal sheets 58 inserted in the lower cap 55*b* are deformed to conform to the shape of the main body portion 2 such that the adapter portion 47 is received by the accommodating portion 59. The other projection 61 is also deformed to be fitted into the corresponding mounting groove 54, whereby the main body portion 2 becomes integral with the lower cap 55*b* to form a unitary assembly.

The surgeon 6 then makes the following preparations for his surgical operation. To make a diopter adjustment for the eyepiece 51 provided on the device 48 for examination by an assistant, the surgeon 6 rotates the eyepiece cover portion 66 of the cover 60 around the axis $O_4$ relative to the second cover portion 63, whereupon the diopter adjusting ring 50 of the eyepiece 51 fitted into the eyepiece cover portion 66 rotates together with the latter relative to the lens barrel 49 so as to adjust the diopter of the eyepiece 51 to the value the surgeon 6 desires. At the same time, the diopter adjusting ring 50 is moved along the axis $O_4$ relative to the lens barrel 49 but the bellows 65 provided on the third cover portion 67 will deform accordingly and, hence, the diopter adjusting ring 50 remains at all times integral with the eyepiece cover portion 66. If the surgeon 6 while performing the operation wants to allow the viewing image from the eyepiece 51 to rotate about the axis $O_4$, he may rotate the rotator ring 52 through the second cover portion 64 with respect to the device 48 on which said rotator ring 52 is provided, whereupon the second cover portion 64 also rotates with respect to the first and third cover portions 63 and 67.

The fourth embodiment described above can be realized by a simple construction in that the mounting groove 53 is provided on the lens mount 3 whereas the mounting grooves 54 are provided on the main body portion 2. The conventional sterilizable caps have had the problem that if they are made of elastic materials in large size, they are so unstable in shape that they cannot be easily mounted over the microscope for operation nor can they be brought into intimate contact with the latter. However, according to the fourth embodiment, metal sheets 58 are inserted in the sterilizable lower cap 55*b* which is large enough to completely cover the main body portion 2 of the microscope for operation body 1 and this enables the lower cap 55*b* to be sterilized with its shape so deformed as to permit effective sterilization. In addition, both the lower cap 55*b* and the metal sheets 58 can be deformed to the shape of the main body portion 2 and, hence, the lower cap 55*b* can be brought into intimate contact with the main body portion 2.

In the fourth embodiment, the first to the third cover portion of the cover 60 that can be mounted over the device 48 for examination by an assistant each have a leaf spring inserted therein and each of them is provided with slit 68 that can be opened wide enough to facilitate their mounting over the device 48; hence, the cover 60 can not only be mounted easily over the device 48 but also provides intimate contact with the latter.

If desired, the metal sheets 58 inserted in the lower cap 55*b* may be formed of a shape-memory alloy having such a composition that, when exposed to a sterilizing high temperature, it will deform to a shape that permits easy mounting but at the normal use temperature, it will deform to the shape of the microscope for operation body 1 consisting of the main body portion 2 and the lens mount 3, whereby the lower cap 55*b* can be effectively retained on the microscope for operation body 1 by the self-clamping force of the alloy.

Figure 21:
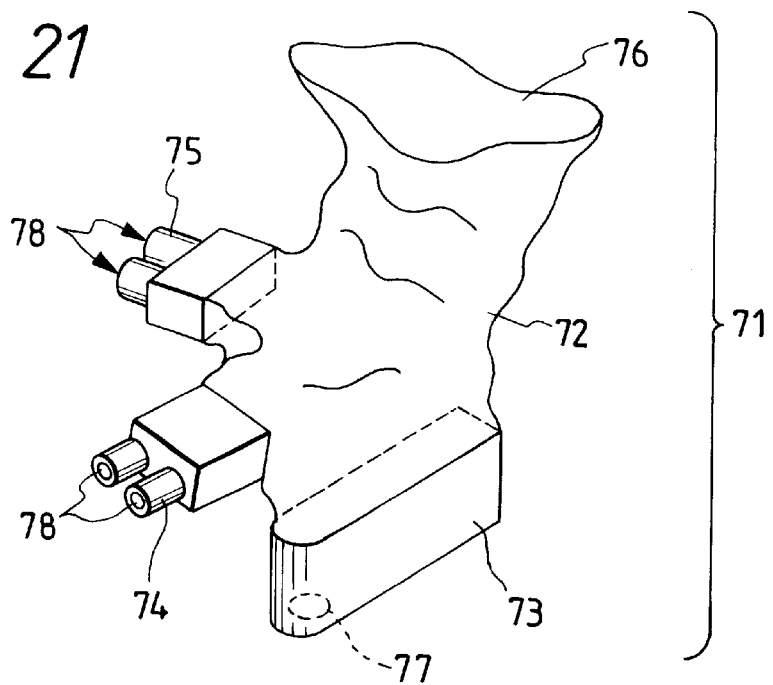
FIG. 21 is a perspective view of a sterile drape according to a fifth embodiment of the invention.
Figure 22:
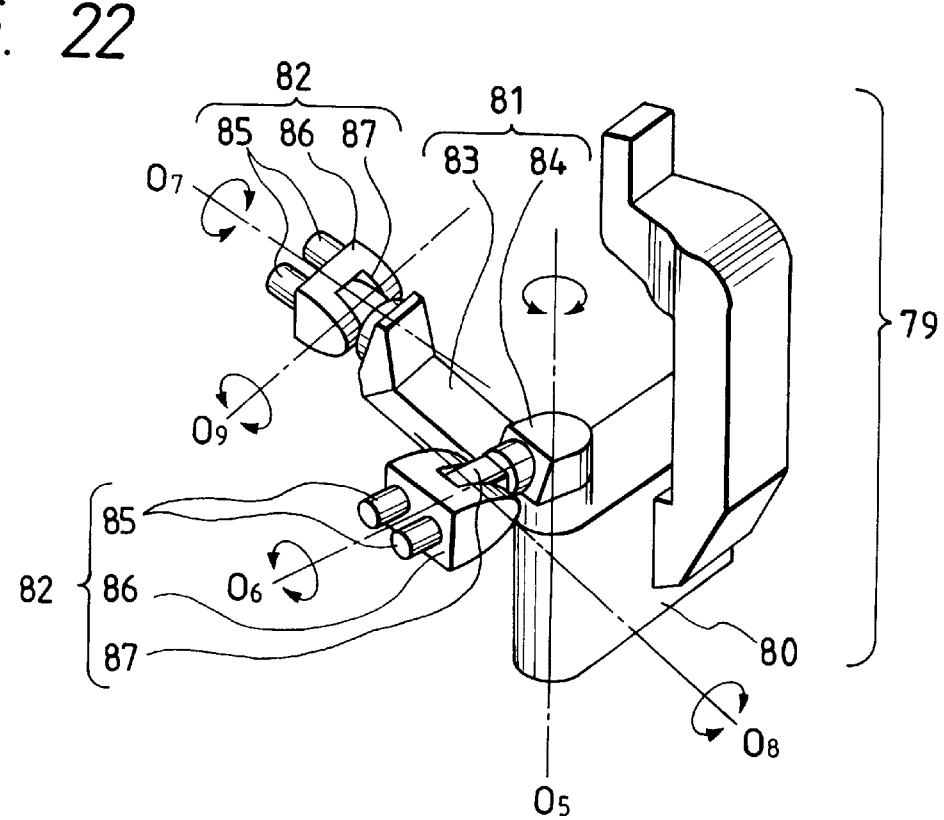
FIG. 22 is a perspective view of a microscope for operation for use in the fifth embodiment.

FIGS. 21–23 show a fifth embodiment of the invention. FIG. 21 shows the overall construction of a sterile drape that can be sterilized or disinfected and that is to be placed over a microscope for operation body which will be described hereinafter. The sterile drape 71 consists of two major parts, a deformable part 72 and a plurality of cap portions 73, 74 and 75. The deformable part 72 is made of a deformable soft material such as a vinyl resin or fabrics and corresponds to the moving parts of a microscope for operation which are capable of changing in exterior shape when the drape has been mounted over the microscope, and the cap portions 73–75 correspond to the other parts of the microscope which will not change in exterior shape and they are identical in interior shape to such non-moving parts of the microscope and are made of an elastic material such as rubber.

The deformable part 72 of the drape 71 has an opening 76 that is large enough to permit the drape to be smoothly mounted over the microscope for operation. The cap portion 73 is provided with an objective window 77 in such a position that the rays of viewing light will not be blocked when the drape is mounted over the microscope for operation. Similarly, the cap portions 74 and 75 each have ocular windows 78 through which the rays of light emerging from the microscope for operation are guided to the surgeon without any interference.

FIG. 22 shows the construction of the microscope for operation over which the sterile drape 71 is to be mounted. Numeral 79 refers to the microscope that is connected to arms (not shown) capable of three-dimensional movements to be fixed in a desired position. The microscope 79 consists of a body 80 containing an objective lens and zooming optics, an intermediate lens mount 81 for splitting a viewing beam of light from the body 80 into two beamlets, and two ocular lens mounts 82.

The intermediate lens mount 81 consists of two parts 83 and 84; the intermediate lens mount 83 is for exclusive use by an assistant and held to be rotatable about the optical axis $O_5$ extending from the object to the objective lens with respect to the body 80, and the intermediate lens mount 84 is for exclusive use by the surgeon and held to be rotatable about the optical axis $O_5$ with respect to the intermediate lens mount 83. The ocular lens mount 82 are held to be rotatable about the axes $O_6$ and $O_7$ with respect to the intermediate lens mounts 84 and 83, respectively. Each ocular lens mount 82 consists of eyepieces 85, a main body portion 86 and a mounting portion 87, and the main body portion 86 is adapted to be rotatable about the axis $O_8$ or $O_9$ with respect to the mounting portion 87.

Consider here the case where the sterile drape 71 having the construction described above is mounted over the microscope for operation 79 such that the latter can be used in a sterile condition. With the opening 76 wide open and facing up, the sterile drape 71 is slipped over the microscope 79 form below. Then, the cap portion 73 is fitted over the body 80 and secured by its resiliency to the latter.

Subsequently, the cap portions 74 and 75 are fitted over the ocular lens mounts 82 and similarly secured by their resiliency to the latter. The cap portion 73 is identical in shape to the body 80 whereas the cap portions 74 and 75 are identical in shape to the ocular lens mounts 82. These cap portions can be mounted in such a way that the objective window 77 provided in the cap portion 73 will not block the rays of light passing through the objective lens (not shown) provided on the body 80 and that the ocular windows 78 provided in the cap portions 74 and 75 will not block the rays of light passing through the eyepieces 85.

If the surgeon while preforming the operation grasps the ocular lens mount 82 and moves them about the axes $O_6$–$O_9$ through the microscope 79, the deformable part 72 of the drape 71 will deform such that the ocular lens mounts 82 can be moved to the position the surgeon desires.

According to the fifth embodiment described above, the drape 71 is made as an integral unit of the deformable part 72 and the non-deformable cap portions 73, 74 and 75; hence, it can be easily mounted over the microscope for operation 79 and yet the number or amount of loose portions of the drape can be reduced compared to the conventional drape which is solely composed of deformable parts. In addition, the non-deformable cap portions 73, 74 and 75 are secured to the microscope 79 by the elastic deformation of these cap portions and, hence, there is no need to provide dedicated mounting means on existing microscope for operations.

As a further advantage, the drape 71 is made of a material that permits repeated use after resterilization and this contributes to a lower running cost than do disposable drapes. If desired, the opening 76 of the deformable part 72 may be equipped with a fastener mechanism which, as shown in FIG. 23, allows the opening 76 to be wide open for mounting the drape over the microscope but which constricts the opening after the mounting operation ends. This facilitates the procedure of mounting the drape over the microscope 79 and offers the added advantage of reducing the number or amount of loose portions of the deformable part 72 that remain after the drape has been mounted over the microscope while precluding the interference of surgical operations by the deformable portion 72.

FIGS. 24–33 show a sixth embodiment of the invention and the parts or components that are identical to those used in the fifth embodiment are identified by like numerals.

FIG. 24 shows a drape generally indicated by 89 that can be mounted over the microscope 79 and, as in the prior art, it is made of a very thin sheet of a deformable material such as a vinyl resin and has been preliminarily sterilized or disinfected. The conventional drape has perforations or some other tear portions in areas that are to be mounted over eyepieces 85 but no such tear portions are required for the drape 89 which is used in the sixth embodiment of the invention.

A sterile cap that can be mounted over the microscope 79 will now be described with reference to FIG. 25. The sterile cap indicated by 90 is a separate member from the drape 89 and it is formed of a non-deformable material such as rigid plastics, having an interior shape generally identical to the microscope body 80.

The sterile cap 90 has a pair of resilient, deformable tabs 91 provided at both lateral edges. The cap 90 is also provided with an objective window 92 which, when the cap is mounted over the microscope body 80, will not block the rays of light passing through the objective lens (not shown) provided on the microscope body 80.

As shown in FIG. 26, a tapered portion 93 serving as a cutter is provided on the inner surface of the cap 90 along the entire peripheral edge of the objective window 92. Also provided within the cap 90 is an accommodating portion 94 which can receive any of the loose portions of the drape 89 when said cap has been mounted over the microscope body 80.

Turning now back to FIG. 25, numeral 95 refers to sterile caps that are also separate from the drape 89 and which are formed of a non-deformable material such as rigid plastics, having an interior shape identical to the ocular lens mounts 82. The sterile caps 95 each have a resilient tab 96 at a lateral edge.

Indicated by 97 are sterile caps that are in a cylindrical form having interior shape identical to the eyepiece 85 and that are made of a non-deformable material such as rigid plastics. As shown in FIG. 27, each sterile cap 97 has a tapered potion 98 at an end that serves as a cutter.

FIG. 28 shows the microscope body 80 over which the sterile cap 90 can be mounted, as well as the ocular lens mount 82 over which either sterile cap 95 or 97 can be mounted. The structural features other than those shown in FIG. 28 are identical to what is shown in FIG. 22 in connection with the fifth embodiment and, hence, well not be described again. The microscope body 80 has two retaining portions 99, one each on a lateral side. When the sterile cap 90 is mounted over the microscope body 80, the retaining portion 99 will engage elastically the tabs 91 on the cap 90 such that the latter is held in position. The retaining portions 99 are hence located in positions that correspond to the tabs 91.

The ocular lens mount 82 has a retaining portion 100 which, when the sterile cap 95 is mounted over the ocular lens mount 82, engages elastically the tab 96 on the cap 95 such that the latter is held in position. The retaining portion 100 is hence located in a position that corresponds to the tab 96.

FIG. 29 shows a cross-sectional shape of one of the eyepieces 85 held in the ocular lens mount 82. As shown, the eyepiece 85 has a groove 101 formed around its base. A similar groove (not shown) is formed around the objective lens held in the microscope body 80. The groove 101 is of the same size as the tapered portion 98 provided on the sterile cap 97, and the groove around the objective lens on the microscope body 80 is of the same size as the tapered portion 93 provided on the sterile cap 90.

The method of mounting the drape 89 over the microscope is the same as in the case of the conventional drape and hence need be not described here. All the steps of the following procedure will be performed with the drape 89 having been mounted on the microscope. After the drape 89 has been mounted over the microscope 79 as shown in FIG. 30, sterile caps 95 are fitted over the ocular lens mounts 82 in such a way that the tab 96 on each cap 95 is oriented in the same direction as the retaining portion 100 on each ocular lens mount 82. As a result, the tabs 96 deform elastically to engage the respective retaining portions 100, whereby the sterile caps 95 are secured to the ocular lens mounts 82.

Figure 31A:
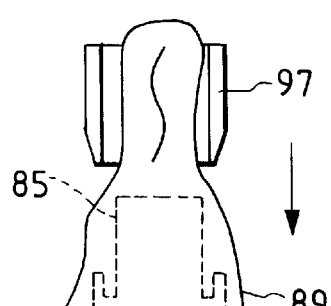
FIG. 31 illustrates an operating mode of the sixth embodiment.
Figure 31B:
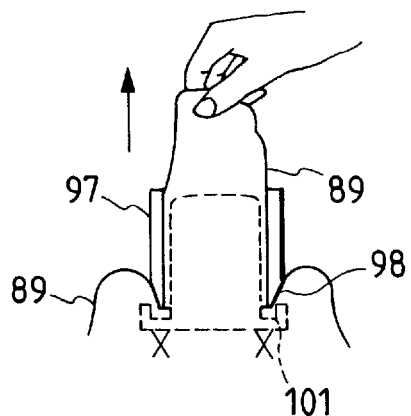

Then, as shown in FIG. 31a, the caps 97, with the tapered portion 98 facing down, are fitted over the eyepieces 85 through the drape 89. As a result, the drape 89 is pinched between the groove 101 on the eyepiece 85 and the sterile cap 97 (see FIG. 31b) and part of the drape 89 is severed by the tapered portion 98 serving as a cutter. By removing the severed part of the drape 89, a viewing optical path is insured that connects between the eyepiece 85 and the surgeon.

Figure 32:
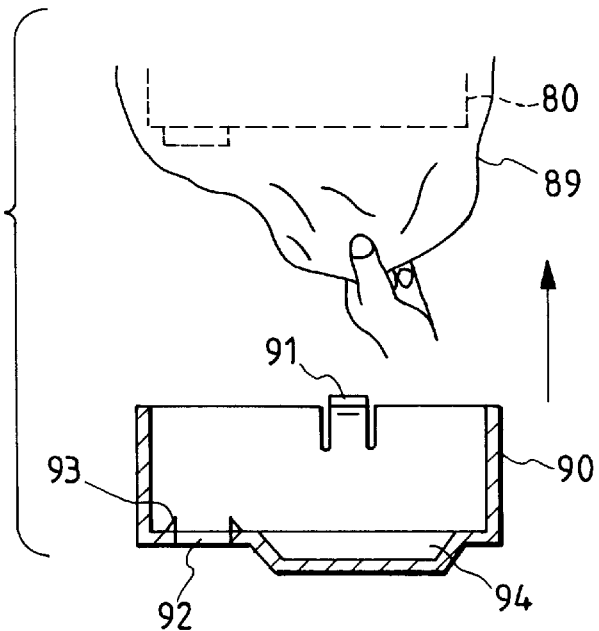
FIG. 32 illustrates another operating mode of the sixth embodiment.
Figure 33:
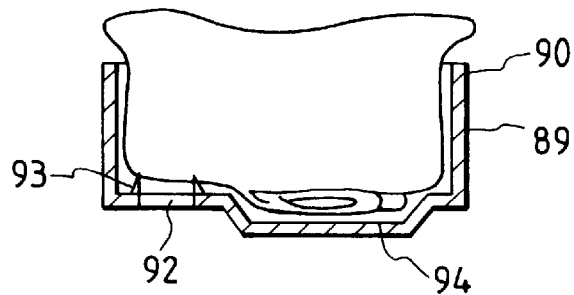
FIG. 33 is a section showing how the sterile drape is accommodated in one of the caps according to the sixth embodiment.

In the next step, the sterile cap 90 is mounted over the microscope body 80 with any loose portions of the drape 89 being held together to come below the microscope 80 as shown in FIG. 32. As a result, the tabs 91 on the sterile cap 90 will deform elastically to engage the respective retaining portions 99 on the microscope body 80, whereby the sterile cap 90 is secured to the microscope body 80. At the same time, any loose portions of the drape 89 that have been held together below the microscope 80 will be received by the accommodating portion 94 of the sterile cap 90, as shown in FIG. 33.

In addition, as in the case of mounting the sterile caps 97 over the eyepieces 85, the drape 89 is pinched between the tapered portion 93 around the objective window 92 and the groove around the objective lens on the microscope body 80, and part of the drape 89 is severed by the tapered portion 93 serving as a cutter. By removing the severed part of the drape 89, the rays of light passing through the objective lens on the microscope body 80 are insured.

According to the sixth embodiment described above, the deformable drape 89 is provided as a separate member from the non-deformable sterile caps 90, 95 and 97 and this permits existing drapes to be used as such. In the prior art, any loose portions of the drape 89 have been brought into intimate contact with the microscope body 80 and the ocular lens mounts 82 with the aid of rubber bands and other binding means. In the sixth embodiment, the use of the non-deformable sterile caps 90, 95 and 97 ensures that loose portions of the drape 89 can be positively eliminated by any person. As a further advantage, the sterile caps 90 and 97 are provided with means for cutting the drape 89 after it has been mounted over the microscope and this not only facilitates the drape cutting operation but also improves its reliability such that unlike in the prior art method which severs the drape 89 along tear lines such as perforations, there is no possibility that the drape is inadvertently severed while it is being mounted over the microscope for operation.

Figure 34:
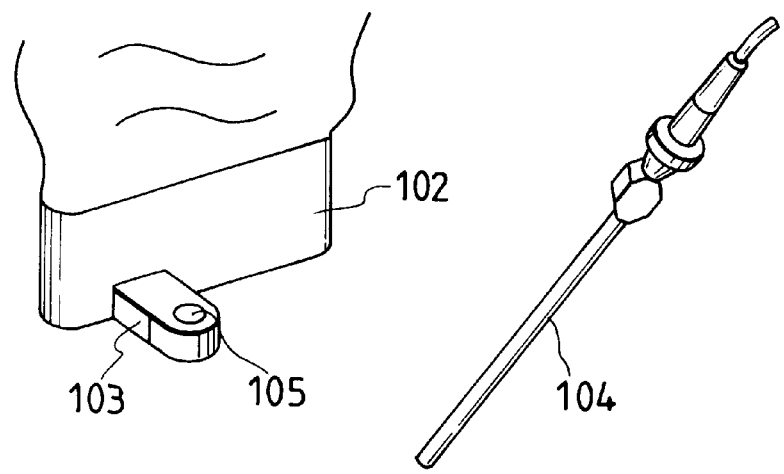
FIG. 34 shows in perspective a sterile cap according to a seventh embodiment of the invention, together with a surgical instrument to be retained by the cap.

FIG. 34 shows a seventh embodiment of the invention and the parts or components that are identical to those used in the sixth embodiment are identified by like numerals and will not be described again. Numeral 102 refers to a sterile cap 90 equivalent to the sterile cap 90 used in the sixth embodiment. As shown, the sterile cap 102 has a retaining portion 103 with a hole 105 through which a surgical instrument 104 can be retained and fixed.

The seventh embodiment offers the advantage that after the sterile cap 102 is secured to the body 80 of the microscope 79 by the same method as employed in the sixth embodiment, a surgical instrument 104 to be used by the surgeon in addition to the microscope 79, for example, an endoscope that has already been sterilized or disinfected by another method is inserted through the hole 105 so that it is secured to the sterile cap 102, hence to the microscope 79.

According to the seventh embodiment, the sterile cap 102 is provided with the retaining portion 103 for holding the surgical instrument 104 by taking advantage of the fact that said cap 102 is positively secured to the body 80 of the microscope 79 and, hence, the surgical instrument 104 that has been sterilized or disinfected by a different method than has been employed to sterilize or disinfect the cap 102 can be secured to the microscope 79 without the risk of contamination.

Figure 35:
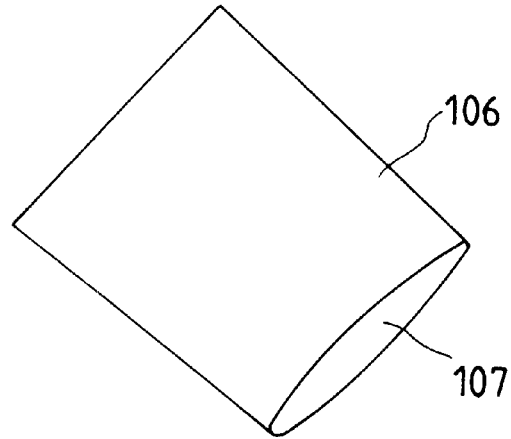
FIG. 35 is a perspective view of a sterile drape according to an eighth embodiment of the invention.
Figure 36:
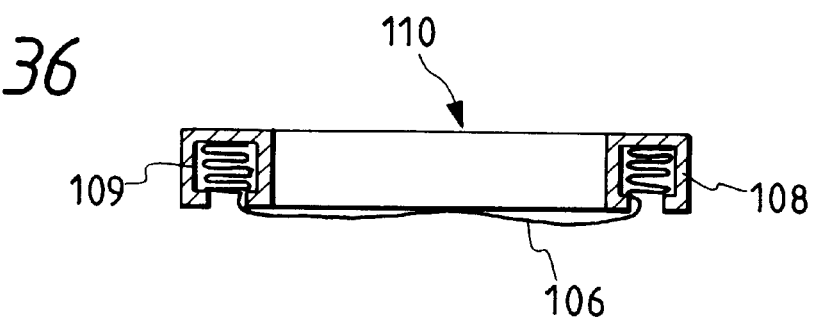
FIG. 36 is a section showing the sterile drape of the eighth embodiment as it is received in an annular accommodating portion.

FIGS. 35 and 36 show an eighth embodiment of the invention and the parts or components that are identical to those used in the fifth, sixth and seventh embodiments are identified by like numerals and will not be described again.

FIG. 35 shows a drape generally indicated at 106 which is in the form of a very thin-walled, deformable and already sterilized or disinfected cylindrical bag. The drape 106 has an opening 107 at an end. Shown by 108 in FIG. 36 is an annular accommodating member that has a cross-sectional shape identical to that of the cylindrical drape 106 and that has already been sterilized or disinfected. It has an accommodating portion 109 for receiving the drape 106 in a folded state with the opening 107 left wide open to a circular form. The opening 107 of the drape 106 and the opening 110 of the annular accommodating portion 108 are of a sufficient size to cover the microscope 79.

If the drape 106 according to the eighth embodiment is to be mounted over the body 80 of the microscope 79 so that the latter can be used in a sterile condition, the surgeon or an authorized operating staff member holds the annular accommodating member 108 and slips it over the whole part of the microscope 79 ranging from its body 80 to the arms (not shown) capable of three-dimensional movements to be fixed in a desired position by passage through the opening 107 of the drape 106 as it is unfolded progressively. Thereafter, the procedures adopted in the sixth embodiment are followed to mount the sterile caps 90, 95 and 95 over the associated parts and secured thereto.

Thus, in the eighth embodiment, the deformable drape 106 assumes a simple cylindrical bag shape and it is received in the annular accommodating member 108 which profiles the cross section of the cylindrical bag; therefore, the person who handles the drape 106 can easily distinguish the outer side of the drape from the inner side and the efficiency of the drape mounting operation is very high since the annular accommodating member 108 needs only to be slipped over the microscope 79.

FIGS. 37–40 show a ninth embodiment of the invention and the parts or components that are identical to those used in the fifth to eighth embodiments are identified by like numerals and will not be described again.

Figure 37:
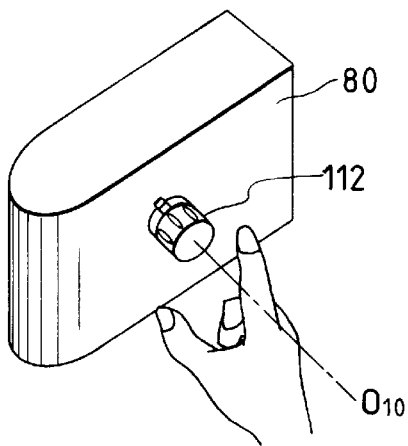
FIG. 37 is a perspective view of a microscope for operation body with a knob for use in a ninth embodiment of the invention.
Figure 38:
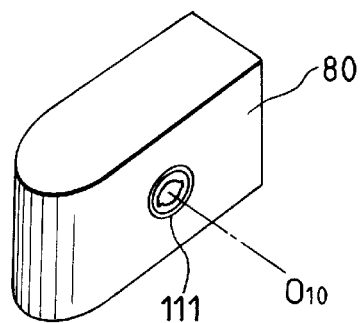
FIG. 38 is a perspective view of the same microscope for operation body without a knob for use in the ninth embodiment.

FIGS. 37 and 38 show the overall construction of the ninth embodiment and numeral 111 refers to a zoom knob mounting hole provided on a lateral side of the microscope body 80. A knob 112 made of a plastic or any other materials that can be repeatedly sterilized or disinfected is detachably mounted in the hole 111.

Figure 39:
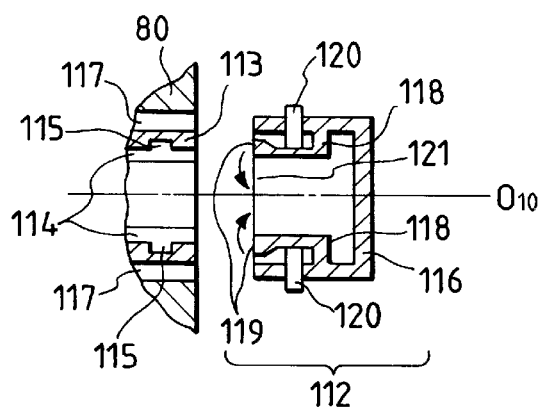
FIG. 39 is a side view showing in longitudinal section a knob on the microscope for operation body for use in the ninth embodiment.

The zoom knob mounting hole 111 and the knob 112 will now be described with particular reference to FIG. 39. Numeral 113 designates a cylindrical tube that can be rotated about the axis $O_{10}$ with respect to the microscope body 80 so that a zooming lens (not shown) contained in it is moved to change the viewing magnification. Cutouts 114 are formed in the inner surface of the cylindrical tube 113 in such a way that they extend parallel to the axis $O_{10}$ and each cutout 114 in turn has a dip 115 formed in a selected area.

We now describe the knob 112 which can be mounted in the zoom knob mounting hole 111. Numeral 116 refers to a grip made of a plastic or any other materials that can be repeatedly sterilized or disinfected. The grip 116 has a cylindrical exterior appearance and can be fitted into a gap 117 between the microscope body 80 and the cylindrical tube 113. Hooks 118 capable of elastic deformation that have the same shape as the cutouts 114 are provided on the inner surface of the grip 116 in positions that correspond to the cutouts 114. Each hook 118 has a projection 119 at the distal end that has the same shape as the dip 115 provided in each cutout 114. The grip 116 is also provided with buttons 120 which, when depressed, cause the hooks 118 to be deformed elastically in directions indicated by arrows 121.

Figure 40:
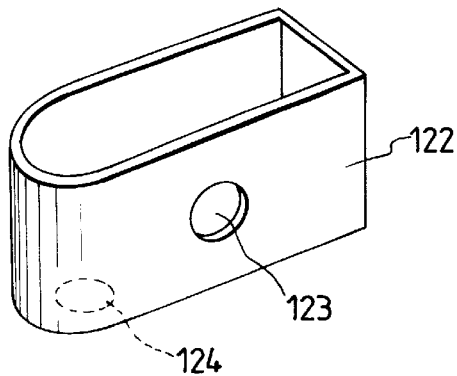
FIG. 40 is a perspective view of a sterile cap according to the ninth embodiment.

FIG. 40 shows a sterile cap portion 122 that can be mounted over the microscope body 80. The structure and shape of the part by which the cap portion 122 is to be mounted over the microscope body 80 are substantially the same as for the cap portion 73 already described in connection with the fifth embodiment, so these aspects will not be described here. The sterile cap portion 122 which is equivalent to the cap portion 73 is fitted with the deformable part 72 of the sterile drape 71 as in the fifth embodiment.

The sterile cap portion 122 has a mounting hole 123 provided on a lateral side in the position that corresponds to the zoom knob mounting hole 111 in the microscope body 80. The mounting hole 123 is of a sufficient size that permits the insertion of the knob 122. As in the foregoing embodiments, the sterile cap portion 122 is provided with an objective window 124 that will not block the rays of light passing through the objective lens (not shown) provided on the microscope body 80.

If the sterile drape 71 including the already sterilized or disinfected cap portion 122 and the knob 112 are to be mounted over the microscope 79 so that the latter can be used in a sterile condition, the drape 71 may be mounted and the sterile cap portion 122 secured to the microscope body 80 by performing the same procedure as in the fifth embodiment.

In the next step, the knob 112 which has already been sterilized or disinfected as it is mounted in the hole 123 in the sterile cap portion 122 is inserted into the zoom knob mounting hole 111 in the microscope body 80 in such a way that the cutouts 114 are in registry with the hooks 118 on the knob 112. In this case, the projections 119 of the hooks 118 contact the cutouts 114, whereupon the hooks 118 will deform elastically in the directions of arrows 121.

As the knob 112 is further pushed into the zoom knob mounting hole 111, the projections 119 will rest in the dips 115 of the cutouts 114, whereupon the resilient hooks 118 will deform in opposite directions to arrows 121, causing the dips 115 to mesh with the projections 119. As a result of this action, the microscope body 80 has the knob 112 secured in position, whereby the microscope 79 is entirely covered with the sterile drape 71 including the cap portion 122 and the knob 112 without leaving no part exposed in a non-sterile and hence contaminated condition.

If the surgeon, while performing the surgical operation, wants to change the viewing magnification, he may simply grasp the knob 112 and rotate it about the axis $O_{10}$. Since the cutouts 114 formed on the inner surface of the cylindrical tube 113 are identical in shape to the hooks 118 provided on the knob 112, the rotation of the knob 112 will be directly transmitted to the cylindrical tube 113. In addition, the dips 115 in the cutouts 114 mesh with the projections 119 of the hooks 118; this insures that the knob 112 will not be disengaged from the microscope body 80 even if the surgeon inadvertently pulls the knob 112 in a direction parallel to the axis $O_{10}$ with respect to the microscope body 80.

In order to remove the sterile drape 71 including the sterile cap portion 122 and the knob 112 from the microscope 79 after the surgical operation ends, the surgeon or an authorized operating staff member may depress the buttons 120 on the knob 112 radially inward, whereby the hooks 118 are deformed elastically in the directions of arrows 121. Then, with the hooks 118 having been deformed elastically by the buttons 120, the knob 112 is pulled out in a direction parallel to the axis $O_{10}$ with respect to the microscope body 80, whereupon it can be separated from the knob 112.

In the ninth embodiment, the knob 112 which would otherwise interfere with the operation of mounting the sterile cap portion 122 over the microscope body 80 is adapted to be detachable and this contributes greatly to an improvement in the efficiency of the mounting operation. In addition, the knob 112 can be sterilized repeatedly and is formed as part of the sterile cap portion 122; hence, the sterile cap portion 122 can be rendered in a sufficiently smaller and lighter entity that the microscope for operation which is covered with that cap portion can work to exhibit its intended performance.

Figure 41:
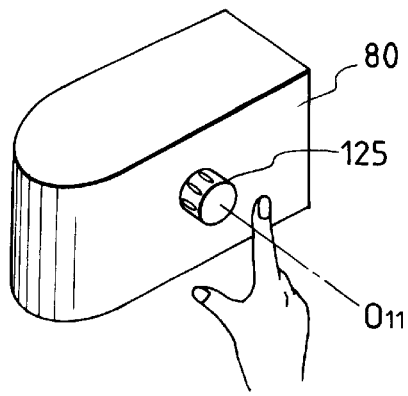
FIG. 41 is a perspective view of a microscope for operation body for use in a tenth embodiment of the invention.

FIGS. 41 and 42 show a tenth embodiment of the invention and the parts on components that are identical to those used in the fifth to ninth embodiments are identified by like numerals.

FIG. 41 shows the overall construction of the tenth embodiment. As shown, the microscope body 80 has a zooming knob 125 on a lateral side which, when rotated about the axis $O_{11}$ with respect to the microscope body 80, will move the zoom lens (not shown) in the microscope body 80 to change the viewing magnification. The zooming knob 125 is so adapted that when depressed relative to the microscope body 80 in a direction parallel to the axis $O_{11}$, it will either project beyond or become flush with the outer surface of the microscope body 80.

We now describe the zooming knob 125 more specifically with reference to FIG. 42. The microscope body 80 contains a lock portion 126 which is mounted rotatably about the shaft $O_{12}$ which is normal to the paper. The lock portion 126 is provided with a working arm 127. The lock portion 126 is also connected to an end of a coil spring 128 that is fixed rotatably about the shaft $O_{13}$ which is also normal to the paper. The other end of the coil spring 128 is fixed to part of the microscope body 80 so that a force is always at work to compress the coil spring 128.

The zooming knob 125 is provided with a spring receptacle 129, which supports an end of a compressive spring 130, the other end of which is fixed to the microscope body 80. The side wall of the spring receptacle 129 has a hook receptacle 131 in the form of an engaging hole. The lock portion 126 has a hook 132 capable of engagement with the hook receptacle 131. Numeral 133 refers to a stopper that restricts the rotation of the lock portion 126 about the shaft $O_{12}$. Numeral 134 refers to a sterile cap that has the same shape as the zooming knob 125 and that can be fitted over the zooming knob 125. This cap can be sterilized repeatedly.

If the sterile drape 71 including the already sterilized or disinfected cap portion 122 and the sterile cap 134 are to be mounted over the microscope 79 so that the latter can be used in a sterile condition, the zooming knob 125 is first pushed into the microscope body 80 so as to compress the spring 130 in a direction parallel to the shaft $O_{11}$, whereupon the spring receptacle 129 pushes the working arm 127 on the lock portion 126, which then rotates about the shaft $O_{12}$ in the direction of arrow 135.

Figure 42A:
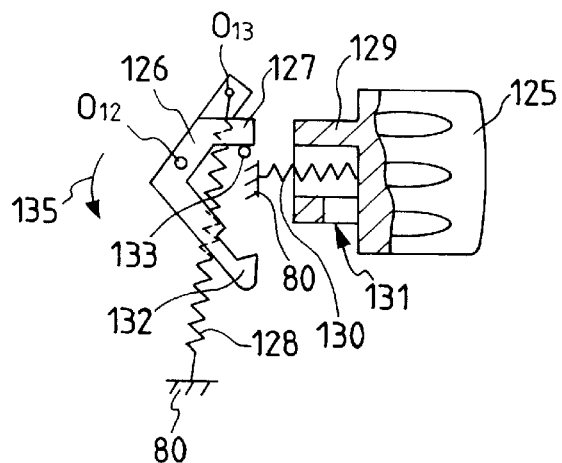
FIG. 42 a set of side views showing in longitudinal section a zooming knob in the tenth embodiment.
Figure 42B:
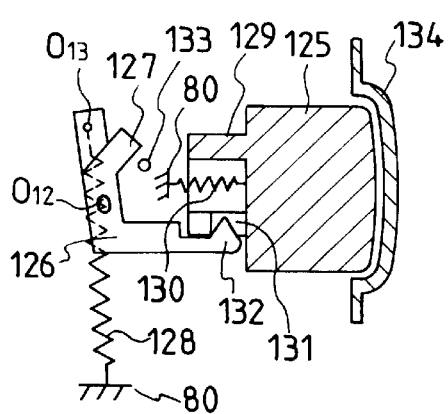

As the rotating shaft $O_{13}$ of the coil spring 128 passes the point of its inflection, the tensile force of the coil spring 128 causes the lock portion 126 to rotate about the shaft $O_{12}$ in the direction indicated by arrow 135. Then, the hook 132 of the lock portion 126 engages the hook receptacle 131 in the spring receptacle 129, so the zooming knob 125 will be fixed in a plane flush with the outer surface of the microscope body 80 as shown in FIG. 42b.

Subsequently, the sterile drape including the sterile cap portion is mounted over the microscope body 80 and the sterile cap portion 122 is secured to the latter, as in the ninth embodiment. If the zooming knob 125 is again pushed into the microscope body 80 in a direction parallel to the axis $O_{11}$, the hook 132 is pushed by the hook receptacle 131 until the rotating shaft $O_{13}$ of the coil spring 128 again passes its point of inflection, whereupon the tensile force of the coil spring 128 will cause the lock portion 126 to rotate about the shaft $O_{12}$ in opposite direction to arrow 135 until it contacts the stopper 133. As a result, the hook 132 is no longer in engagement with the hook receptacle 131 and the reverting action of the compressive spring 130 will allow the zooming knob 125 to project again beyond the outer surface of the microscope body 80 as shown in FIG. 42a. Finally, the preliminarily sterilized or disinfected cap 134 is mounted over the zooming knob 125, whereby the whole part of the microscope 79 can be covered with sterile portions.

After the surgical operation, the sterile drape 71 including the sterile cap portion 122 and the sterile cap 134 for fitting over the zooming knob may be removed by reversing the sequence of steps employed to mount those members over the microscope 79.

Therefore, in the tenth embodiment, the projection of the zooming knob 125 which would otherwise interfere with the operation of mounting the sterile cap portion 122 over the microscope body 80 can be eliminated and this contributes greatly to an improvement in the efficiency of the mounting operation. In addition, the sterile cap portion 122 can be rendered in a sufficiently smaller and lighter entity that the microscope 79 which is covered with that cap portion can work to exhibit its intended performance. As a further advantage, the zooming knob 125 can be advanced to or retracted from the microscope body 80 but the two members are by no means separable and, hence, there is no possibility for the surgeon or any authorized operating staff member to lose the zooming knob 125 inadvertently.

According to the first to the tenth embodiment of the invention described above, there could be provided microscope for operations or sterile drapes having the constructions specified in the following Notes.

i) A microscope for operation comprising a microscope body, a sterilizable cap capable of covering the whole part of said microscope body, and a retaining portion for retaining said cap which is provided on said microscope body.

ii) A microscope for operation as recited in i), wherein either one of said microscope body retaining portion and the portion where said cap is to be mounted is projecting while the other is recessed.

iii) A microscope for operation as recited in i), wherein said retaining portion is projecting as a functional knob for manipulating said microscope body.

iv) A microscope for operation as recited in i), wherein said retaining portion is composed of an electromagnetic member provided on either one of said microscope body and said cap and a metallic member provided on the other.

v) A microscope for operation as recited in iv), wherein said electromagnetic member is an electromagnetic coil.

vi) A microscope for operation as recited in iv), wherein said electromagnetic member is a permanent magnet.

vii) A microscope for operation as recited in i), wherein said cap is formed of an elastic material that can be sterilized by autoclaving.

viii) A microscope for operation as recited in i), wherein said cap has portions that are to cover the moving parts of said microscope body and which are adapted to be movable.

ix) A microscope for operation as recited in i), wherein said cap is split into two parts.

x) A microscope for operation as recited in i), wherein said cap has deformable flexible portions that correspond to the moving parts of the microscope body.

xi) A microscope for operation as recited in i), wherein said cap has a flexible material inserted therein.

xii) A microscope for operation as recited in x), wherein the deformable flexible portions are bellows.

xiii) A microscope for operation as recited in xi), wherein the flexible material is a metal sheet.

xiv) A microscope for operation as recited in i), wherein said cap is principally formed of a hard material that can be sterilized by autoclaving and partly of an elastic material.

xv) A microscope for operation as recited in xv), wherein said cap has a leaf spring inserted therein.

xvi) A microscope for operation as recited in i), wherein said cap has a shape-memory alloy inserted therein or a shape-memory resin mesh incorporated therein.

xvii) A microscope for operation as recited in vii), wherein said elastic material that can be sterilized by autoclaving is rubber.

xviii) A microscope for operation as recited in i), wherein said cap has slits.

xix) A sterilize drape that is to be placed over a microscope for operation so as to keep its outer surfaces in a sterile condition, characterized in that said drape consists of a deformable member placed in areas that correspond to the moving parts of the microscope for operation and a non-deformable member placed in areas that correspond to the non-moving parts of the microscope for operation, said non-deformable member being fixable to the microscope for operation.

xx) A sterile drape as recited in xix), wherein said deformable member is placed at the opening of the drape, said opening being adapted to be adjustable in diameter.

xxi) A sterile drape as recited in xix), wherein said deformable member is a separate entity from the non-deformable member.

xxii) A sterile drape as recited in xxi), wherein said non-deformable member has means for accommodating or breaking the deformable member.

xxiii) A sterile drape as recited in xix) or xxi), wherein said non-deformable member has means for retaining a surgical instrument.

xxiv) A sterile drape as recited in xxii), wherein said deformable member is in a simple tubular form and received in an annular accommodating member that consists of a plurality of cross sections that profile the corresponding cross sections of the tube.

xxv) A microscope for operation having means for eliminating the projection of a manipulating knob that will interfere with the step of securing the non-deformable member recited in xix).

xxvi) A microscope for operation as recited in xxv), wherein said projection eliminating means is composed of a mechanism for mounting or dismounting the manipulating knob.

xxvii) A microscope for operation as recited in xxv), wherein said projection eliminating means is composed of a mechanism for advancing or retracting the manipulating knob.

According to Note XIX, there is provided a sterile drape that is to be placed over a microscope for operation, characterized in that a deformable member is placed in areas that correspond to the moving parts of the microscope for operation whereas a non-deformable member that can be fixed to the microscope for operation is placed in areas that correspond to the non-moving parts of the microscope for operation. When the drape has been placed over the microscope for operation, the non-deformable member is secured to the corresponding parts of the microscope.

According to Note XX, the deformable member is placed at the opening of the sterile drape and said opening is adapted to be adjustable in diameter. The diameter of the opening increases when the drape is being placed over the microscope and decreases after the drape has been placed in position.

According to Note XXI, said deformable member is a separate entity from said non-deformable member, so that after the whole part of the microscope for operation has been covered with the deformable member alone, the non-deformable member is secured to the corresponding parts of the microscope for operation via said deformable member.

According to Note XXII, said non-deformable member has means for accommodating or breaking the deformable member and this ensures that when the non-deformable member is being secured to the microscope for operation via said deformable member, part of the latter is either accommodated in or broken away by the non-deformable member.

According to Note XXIII, said non-deformable member has means for retaining a surgical instrument that has been sterilized by a different method than has used to sterilize the drape and this ensures that after the non-deformable member is secured to a corresponding part of the microscope for operation, the sterilized surgical instrument is secured to the non-deformable member.

According to Note XXIV, said deformable member is in a simple tubular form and received in an annular accommodating member that consists of a plurality of cross sections that profile the corresponding cross sections of the tube. This insures that when the annular accommodating member is slipped over the microscope for operation, the deformable member will progressively be unfolded from the annular accommodating member, thereby covering the microscope for operation.

According to Note XXV, there is provided a microscope for operation having means for eliminating the projection of a manipulating knob that will interfere with the step of securing the non-deformable member and this is capable of eliminating the projection of the manipulating knob on the microscope for operation before the non-deformable member is secured to it.

According to Note XXVI, said means for eliminating the projection of the manipulating knob on the microscope for operation is a mechanism for mounting or dismounting the manipulation knob, so that the manipulation knob can be removed before the non-deformable member is secured to the microscope for operation.

According to Note XXVII, said means for eliminating the projection of the manipulating knob on the microscope for operation is a mechanism for advancing or retracting the manipulation knob, so that the manipulation knob can be depressed to have no projection left before the non-deformable member is secured to the microscope for operation.

The sterile drape recited in Note XIX offers the following advantages: the use of the deformable member ensures the inherent mobility of an existing microscope for operations; the non-deformable member is adapted to have an identical exterior shape to the microscope for operation and this eliminates the formation of loose portions of the drape which has been unavoidable in the prior art; the non-deformable member is adapted to be fixable to the microscope for operation so that the slip problem which has conventionally been encountered during the manipulation of microscope for operations is eliminated; as a result, all of the problems with the prior art can reasonably be solved, thereby contributing to a higher efficiency of surgical operations.

The sterile drape recited in Note XX has an opening that is adapted to be adjustable in diameter and this is effective in compensating for the deterioration in the efficiency of the drape mounting operation which occurs due to the placement of the non-deformable member.

The sterile drape recited in Note XXI has the deformable member provided as a separate entity from the non-deformable member and this guarantees a drape mounting operation that can be performed as efficiently as in the prior art.

The sterile drape recited in Note XXII provides the non-deformable member with means for accommodating or breaking the deformable member and this contributes to a further reduction in the formation of loose portions when the drape is mounted over the microscope for operation. This advantage is achieved even if the deformable member is of a simple shape and, hence, not only can the deformable member be mounted with improved efficiency but also the cost of drape fabrication is reduced. If the non-deformable member is provided with means for breaking the deformable member, the possibility of exerting an unwanted force on the microscope for operation during the drape mounting operation as in the prior art is eliminated, thereby contributing to a smaller chance of failure.

The sterile drape recited in Note XXIII has means of retaining a surgical instrument in the non-deformable member by taking advantage of the fact that said non-deformable member is positively secured to the microscope for operation and, hence, a surgical instrument that has been sterilized by a different method than has been employed to sterilize the drape can be secured to the microscope for operation without the risk of contamination.

The sterile drape recited in Note XXIV not only has the deformable member formed in a simple tubular shape but also contains it in the annular accommodating member which consists of a plurality of cross sections that profile the corresponding cross sections of the tube; therefore, the person who handles the drape can easily distinguish the outer side of the drape from the inner side and, what is more, the efficiency of the drape mounting operation is very high since the annular accommodating member needs only to be slipped over the microscope for operation.

The microscope for operations recited in Notes XXV–XXVII have no projections that would otherwise interfere with the operation of mounting the non-deformable member over the microscope and hence the efficiency of the mounting operation is improved. In addition, the non-deformable member can be rendered in a sufficiently smaller and lighter entity that the inherent performance of the microscope for operations can be fully exploited.

In microsurgery which is performed under examination with microscope for operations, it is common practice to prevent the infection of patients by either covering the microscope for operation with a sterile drape or sterilizing the microscope per se. It is generally known to sterilize the microscope for operation per se by enclosing a specified part of the microscope with a bag incorporating a chemical container, sealing the bag with adhesive tape, and filling the interior of the bag with ethylene oxide gas evaporating from the chemical container. According to the different approach disclosed in Examined Published Japanese Patent Application (kokoku) Hei 3-17493, sterilization is accomplished with a sterilizer provided within a box accommodating a microscope for operation that is formed in a sidewall of an operating room.

A problem with the use of the sterile drape is that the positioning of the microscope body cannot be performed during a surgical operation with the required accuracy because the drape becomes excessively tight in areas near the moving parts of the microscope body supporting device or the surgeon'hand holding the manipulating handle will slip due to the drape.

The problem with the use of ethylene oxide gas is that in order to achieve the intended sterilizing effect, it must be used at 40–60° C. with the pressure being elevated sufficiently to have the gas reach every site that need be sterilized. If sterilization is performed at ordinary temperatures and pressures using a chemical container, the sterilizing effect may be insufficient to guarantee utmost safety in using the treated microscope for operation. A further problem with this approach is that after the sterilizing step, a prolonged stand-by time is required to remove the toxic residual ethylene oxide and hence it is not suitable for use in the case where a number of surgical operations have to be performed.

The proposal made in Examined Published Japanese Patent Publication (kokoku), Hei. 3-17493 also suffers from several disadvantages. First, a special alteration must be made to the operating room in order to provide the sterilizer accommodating box in a sidewall of the operating room. Second, the relative positions of the microscope for operation and bed are fixed so that not all techniques of surgical operations cannot be practiced. Third, the microscope for operation is not movable, so a single unit of microscope for operation cannot be used in more than one operating room. Fourth, the recent advances in the technology of microscope for operations are so rapid that the product cycle is becoming shorter; however, making a substantial alteration each time a new microscope for operation is purchased is not only costly but also inconvenient since no surgical operations can be performed during the alteration work.

Under these circumstances, the present inventors made intensive studies and have successfully developed a new type of microscope for operation that can be positively sterilized within a short time, that is safe to use without the risk of infection and that yet can be used in various locations.

Figure 43:
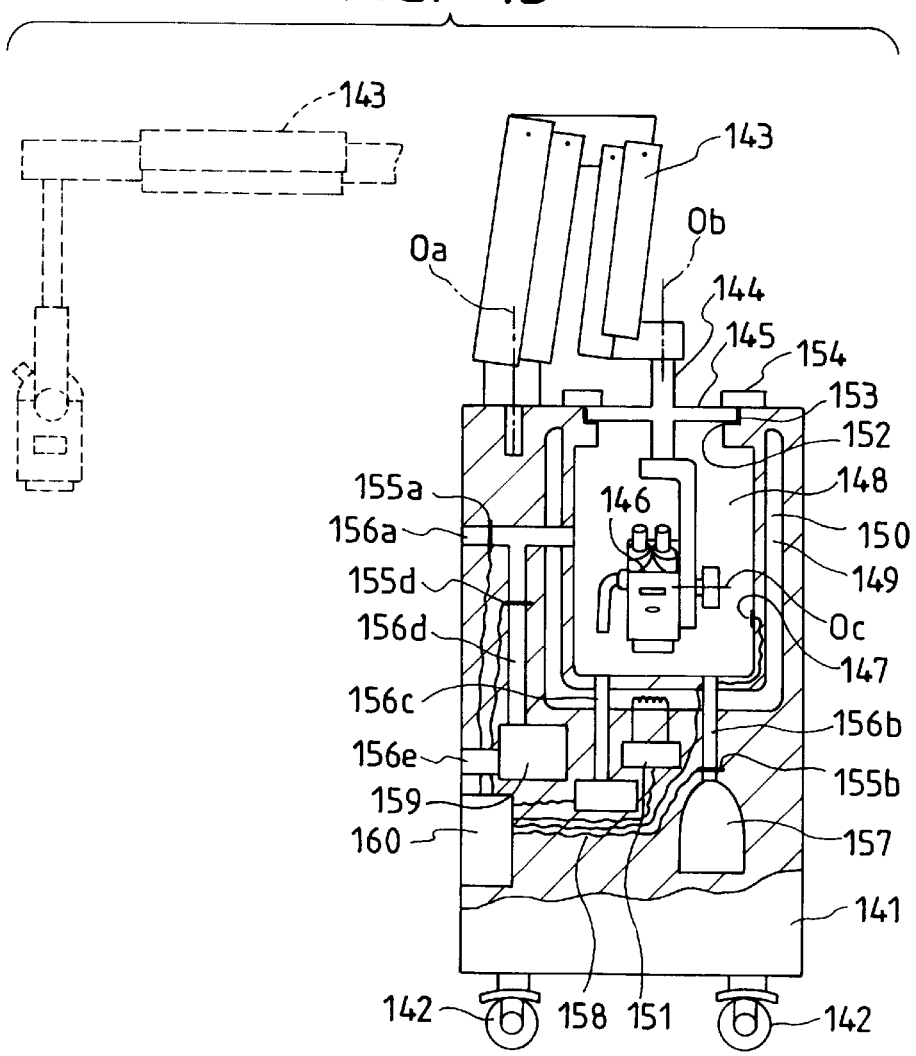
FIG. 43 is a side view showing in longitudinal section an microscope for operation for use in a first disclosure of the invention.
Figure 44:
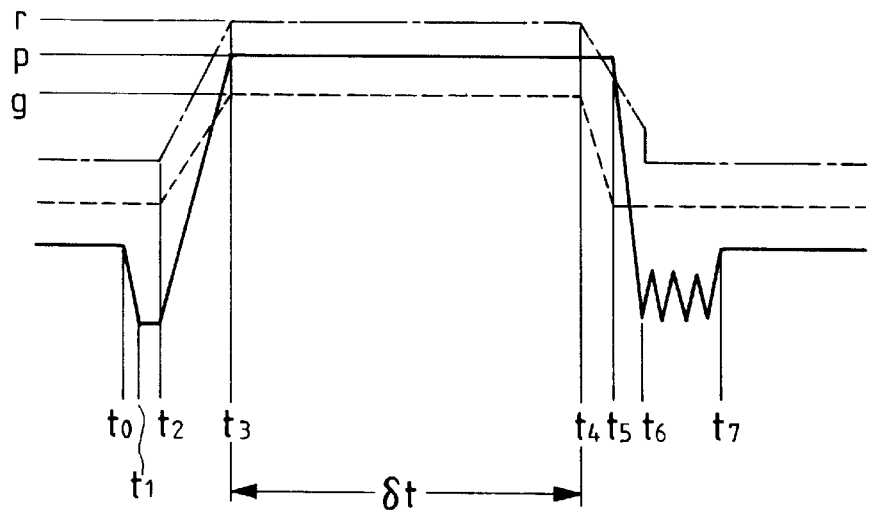
FIG. 44 is a diagram showing the pressure changes that occur within the sterilizing chamber of the microscope for operation in the first disclosure.

FIG. 43 is a sectional view showing the overall construction of a microscope for operation according to a first disclosure of the invention. FIG. 44 is a diagram showing how the pressure in a sterilizing chamber changes in the course of sterilization. As shown in FIG. 43, a housing 141 has casters 142 on the bottom and a two-action pantograph arm 143 is provided on the top in such a way that it is rotatable about the axis Oa. The two-action pantograph arm 143 has a balancing mechanism and a microscope body arm 144 is provided at the distal end in such a way that it is rotatable about the axis Ob. The microscope body arm 144 is fitted with a lid 145 and a microscope body 146 is provided below the lid in such a way that it is rotatable about the axis Oc.

The housing 141 also contains a sterilizing chamber 148 equipped with a multi-sensor 147 capable of temperature, humidity and pressure measurements, as well as a warm water tank 149 provided to surround the sterilizing chamber 148. The warm water tank 149 is equipped with an electric heater 151 for heating an internal liquid 150. The sterilizing chamber 148 has a packing 152 provided on the top, which has an opening 153 of a shape that provides snug fit to the lid 145; clamps 154 for fixing the lid 145 in position are provided near the opening 153.

The sterilizing chamber 148 has pipes 156a, 156b and 156c connected thereto in such a way as to permit the flow of a fluid; the pipes 156a and 156b are fitted with valves 155a and 155b, respectively. The pipe 156a has a pipe 156d connected thereto in a position that is closer to the sterilizing chamber 148 than the valve 155a, and the pipe 156d is fitted with a valve 155d. The pipe 156a opens to the outside of the housing 141, whereas pipes 156b, 156c and 156d are connected to an ethylene oxide gas (hereunder abbreviated as "EOG") container 157, a humidifier 158 and a vacuum apparatus 159, respectively, in such a way as to permit the flow of a fluid. The vacuum apparatus 159 has a pipe 156e that also opens to the outside of the housing 141. Valves 155a, 155b and 155d, as well as sensor 147, electric heater 151, humidifier 158 and vacuum apparatus 159 are electrically connected to a control unit 160.

We now describe the operation of the microscope for operation having the construction outlined above. The first topic to be discussed is making preparations for sterilization. The microscope body 146 which is normally positioned as indicated by a dashed line in FIG. 43 is brought into the sterilizing chamber 148 by means of the two-action pantograph arm 143; thereafter, the lid 145 is fitted into the opening 153 and the microscope body 146 is fixed in position with the lid 145 and the packing 152 having been brought into intimate contact by means of the clamps 154. This completes the process of sealing the interior of the sterilizing chamber 148.

The time profiles of the action and the operation of the sterilizer as it is controlled by the control unit 160 will now be described with reference to FIG. 44. Before t0, valves 155a, 155b and 155d are all closed and vacuum apparatus 159, heater 151 and humidifier 158 are all OFF (this is a so-called "initial state"). At t0 valve 155d is opened and vacuum apparatus 159 is turned on, whereupon the gas in the sterilizing chamber 148 is forced out through pipe 156e so that a vacuum has been created within the sterilizing chamber 148 by the time t1 is reached. Subsequently, at t2, vacuum apparatus 159 is turned off, valve 155d is closed and valve 155b is opened, whereupon EOG is supplied from EOG container 157 into the sterilizing chamber 148. Since gas container 157 has high internal pressure, EOG is kept supplied into the sterilizing chamber 148 after the pressure in it has become more than one atmosphere.

At t2, electric heater 151 also turns on and the increasing heat of the liquid 150 within the warm water tank 149 is transmitted to the sterilizing chamber 148 so that its internal temperature will increase substantially uniformly throughout the interior. In addition, humidifier 158 turns on at t2 and the generated vapor will increase the humidity in the sterilizing chamber 148. When the pressure detected by sensor 147 has reached a preset value p at time t3, valve 155b is closed and the supply of EOG into the sterilizing chamber 148 is stopped so that the internal pressure will level off. At about t3, the temperature and humidity in the sterilizing chamber 148 as detected by sensor 147 also reach respective preset values q and r, whereupon the electric heater 151 and humidifier 158 are turned off.

If the temperature and humidity in the sterilizing chamber 148 drop to second preset values q2 and r2 which are slightly lower than q and r, the electric heater 151 and humidifier 158 are turned on again. Thereafter, the heater 151 and humidifier 158 are cyclically turned on and off between two preset values q and q2, as well as between r and r2 such that the temperature and humidity in the sterilizing chamber 148 are kept at substantially constant levels through the period from t3 to t4 which is spaced from t3 by δt which is the preset time required of sterilization. During this time interval between t3 and t4, the EOG at the appropriate pressure will diffuse to reach every part of the space within the sterilizing chamber 148 such that its interior is held at the temperature and pressure appropriate for sterilization, thereby insuring that the microscope body 146 is thoroughly sterilized. When the sterilization ends at t4, the heater 151 and humidifier 158 are turned off and the interior of the sterilizing chamber 8 is left to cool to an ordinary temperature. At t5, sensor 147 detects this fact and allows valve 155d to open; at the same time, vacuum apparatus 159 is turned on to force all of the gas in the sterilizing chamber 148 to go outside through pipe 156e. At t6, sensor 147 detects the creation of a vacuum in the sterilizing chamber 148 and allows valve 155d to close and valve 155a to open, whereupon the external air will s spontaneously flow into the sterilizing chamber 148 which has a lower pressure than the outside air. However, at this point of time, residual ethylene oxide persists not only on the inner surfaces of the sterilizing chamber 148 but also within or on the outer surfaces of the microscope body 146. Therefore, in order to remove such residual ethylene oxide, aeration is performed by repeating the aforementioned forced discharge and spontaneous suction through a preset number of cycles at preset time intervals until t7, when the sterilization process is complete. The sterilization process is usually accomplished under a high temperature not less than 100° C. and 1 atmospheric pressure, or sometimes under a high pressure.

Thus, the ethylene oxide gas is supplied into the sterilization chamber 148 at the appropriate pressure after all air has been withdrawn from that chamber and its interior is thereafter held at the temperature and humidity suitable for sterilization; hence, not only the exterior but also the interior of the microscope body 146 can be positively sterilized. In addition, the sterilization step is immediately followed by aeration and, hence, there will be no residual ethylene oxide and the microscope for operation can be put to use as soon as the aeration step ends. As a further advantage, the casters 142 provided on the bottom of the housing 141 help move the microscope for operation to every location in a hospital, thereby offering a great convenience in practical applications.

Figure 45:
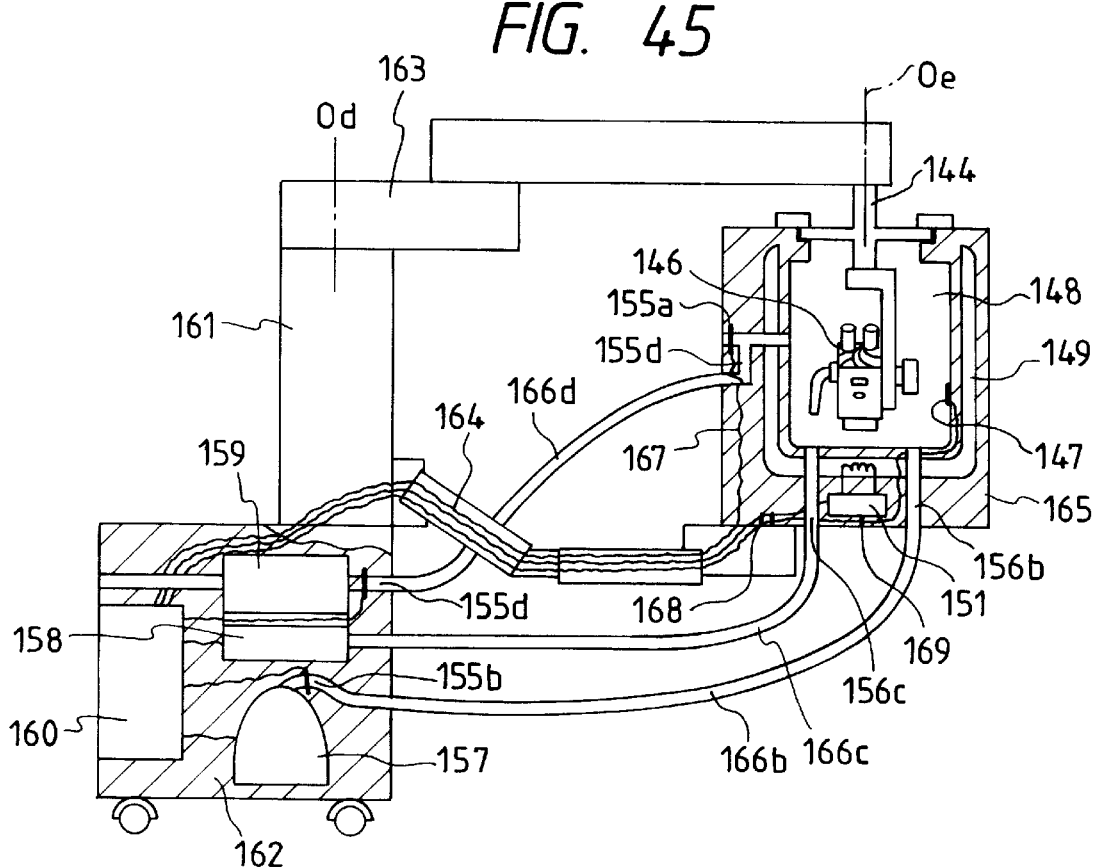
FIG. 45 is a side view showing in longitudinal section a microscope for operation for use in a second disclosure of the invention.

FIG. 45 is a sectional view showing the overall construction of a microscope for operation according to a second disclosure of the invention. The sterilizing apparatus according to the second disclosure has been developed to insure that sterilization as effective as in the case of the first disclosure can be accomplished for microscope for operation even if its body is supported by various structures of arms.

In FIG. 45, the parts or components that are identical to those used in the first disclosure are identified by like numerals and will not be described again. The housing 141 consists of a pole 161 and a base 162 for supporting this pole. The base 162 contains an EOG container 157, a humidifier 158, a vacuum apparatus 159 and a control unit 160. An arm apparatus 163 is mounted at the top end of pole 161 in such a way that it is rotatable about the axis Od, and a microscope body arm 144 is mounted at the distal end of the arm apparatus 163 in such a way that it is rotatable about the axis Oe.

A two-action pantograph arm 164 is secured to the pole 161 at an end and the other end of this pantograph arm is secured to a sterilizing box 165 containing a sterilizing chamber 148, a warm water tank 149 and an electric heater 151. A hose 166d fitted with valve 155d is connected to a pipe 156d at an end and the other end of this hose is connected to the vacuum apparatus 159. One end of a hose 166c is connected to a pipe 156c and the other end of this hose is connected to the humidifier 158. A hose 166b fitted with a valve 155b is connected to a pipe 156b at an end and the other end of this hose is connected to the EOG container 157. Valve 115a, electric heater 151 and sensor 147 are connected to the control unit 160 via cables 167, 168 and 169, respectively, which are contained in the two-action pantograph arm 164.

We now describe the operation of the microscope for operation having the construction outlined above. First, sterilizing box 165 is transferred to the position shown in FIG. 45 by means of the two-action pantograph arm 164 and, thereafter, the microscope body 146 is brought into the sterilizing chamber 148, whose internal space is then sealed. Sterilizing chamber 148 is capable of fluid transfer to and from EOG container 157, humidifier 158 and vacuum apparatus 159 through respective hoses 166b, 166c and 166d such that sterilization is performed by the same procedure as described in the first disclosure.

Thus, in the second disclosure of the invention, even a microscope for operation whose body is supported by various types of arms in order to provide for different capabilities can be sterilized as effectively as in the first disclosure by mounting sterilizing box supporting arm apparatus 163 on the housing 141 in the manner described just above.

Figure 46:
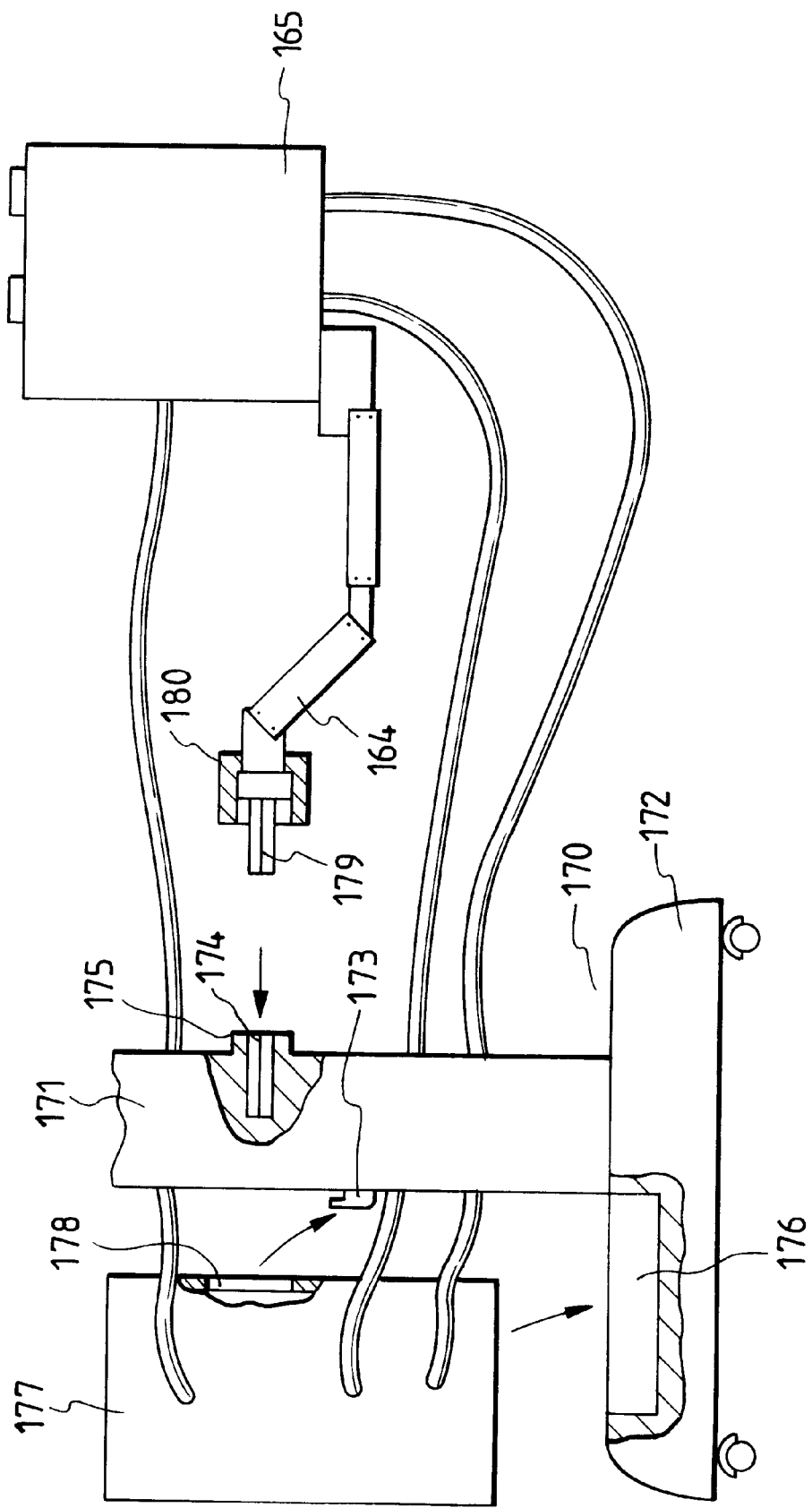
FIG. 46 is a side view showing in longitudinal section an microscope for operation for use in a third disclosure of the invention.

FIG. 46 is a sectional view showing the overall construction of a microscope for operation according to a third disclosure of the invention. The primary objective of the third disclosure is to adapt the sterilizer in the second disclosure such that it can freely be mounted on or dismounted from the microscope body supporting apparatus, thereby increasing the latitude in system selection so as to meet specific user' needs.

In FIG. 46, the parts or components that are identical to those used in the first and second disclosures are identified by like numerals and will not be described again. A stand generally indicated by 170 consists of a pole 171 and a base 172 supporting this pole. The pole 171 is provided with a hook 173, a rectangular hole 174 and an externally threaded portion 175, and a recess 176 is provided in the top surface of the base 172.

The EOG container 157, humidifier 158, vacuum apparatus 159 and control unit 160 are contained in a sterilizing unit 177, which is provided with an slot 178 capable of engagement with the hook 173. The two-action pantograph arm 164 is provided at an end with a rectangular rod portion 179 that is to be fitted into the rectangular hole 174, as well as a fixed ring 180 having a female thread that meshes with the externally threaded portion 175. The other end of the pantograph arm 164 is secured to the sterilizing box 165.

We now describe the procedure of mounting the sterilizer on the pole 171. The sterilizing unit 177 is placed into the recess 176 in the base 17 with care being taken to insure that the slot 178 is in registry with the hook 173. Then, the rectangular rod portion 179 is inserted into the rectangular hole 174 and the fixed ring 180 is threaded over the externally threaded portion 175, whereby the two-action pantograph arm 164 is secured to the pole 171. For dismounting the sterilizer, the order is reversed.

Thus, the sterilizer can be freely mounted or dismounted from the housing and this increases the latitude in system selection to meet specific user'need; for instance, if a surgeon who does not like sterile drapes takes over charge of an operating room in which the use of sterile drapes has been customary, the system can be easily switched to the sterilization of a microscope for operation per se by adding a suitable sterilizer.

According to the first to third disclosures given above, the bodies of microscope for operations can be sterilized so positively that they can be used with utmost safety against infections and, in addition, aeration is completed within such a short time that the microscope for operation can be used as soon as it is sterilized. Moreover, the microscope for operation is adapted to be movable, so it can be used in various locations, which adds to the practical value of the invention.

According to the first to the third disclosure of the invention described above, there could be provided microscope for operations having the constructions specified in the following Notes.

XXVIII) A microscope for operation having a device for supporting its body, characterized in that said supporting device is equipped with a sterilizer.

XXIX) A microscope for operation as recited in xxviii), wherein the pressure of a gas in the sterilizing chamber of said sterilizer is variable.

XXX) A microscope for operation as recited in xxviii), wherein the temperature of a gas in the sterilizing chamber of said sterilizer is variable.

XXXI) A microscope for operation as recited in xxviii), wherein the sterilizing gas used in said sterilizer is ethylene oxide gas.

XXXII) A microscope for operation as recited in xxviii), wherein the sterilizing gas used in said sterilizer is formaldehyde gas.

XXXIII) A microscope for operation as recited in xxviii), wherein said sterilizer is contained in or an integral part of the pole portion of said supporting device.

XXXIV) A microscope for operation as recited in xxviii), wherein said supporting device has an arm of such a structure and a layout the microscope body can be brought into said sterilizing chamber.

XXXV) A microscope for operation as recited in xxxiv), wherein said arm comprises at least two pantograph structures.

XXXVI) A microscope for operation as recited in xxviii), wherein the base portion of said supporting device is fitted with casters for moving said supporting device.

XXXVII) A microscope for operation having a device for supporting its body, characterized by having a first arm for supporting the microscope body and a second arm that is separated from said first arm and that is secured to the pole portion of said supporting device, with a sterilizer being connected to the distal end of said second arm.

XXXVIII) A microscope for operation as recited in xxxvii), wherein said sterilizer consists of two sections, one being a sterilizing chamber connected to the distal end of said second arm and the other being the main body secured to the supporting device, with fluid transfer being effected between said two sections by means of at least one hose.

XXXIX) A microscope for operation as recited in xxxvii), wherein said sterilizer is detachably mounted on said supporting device.

Figure 47:
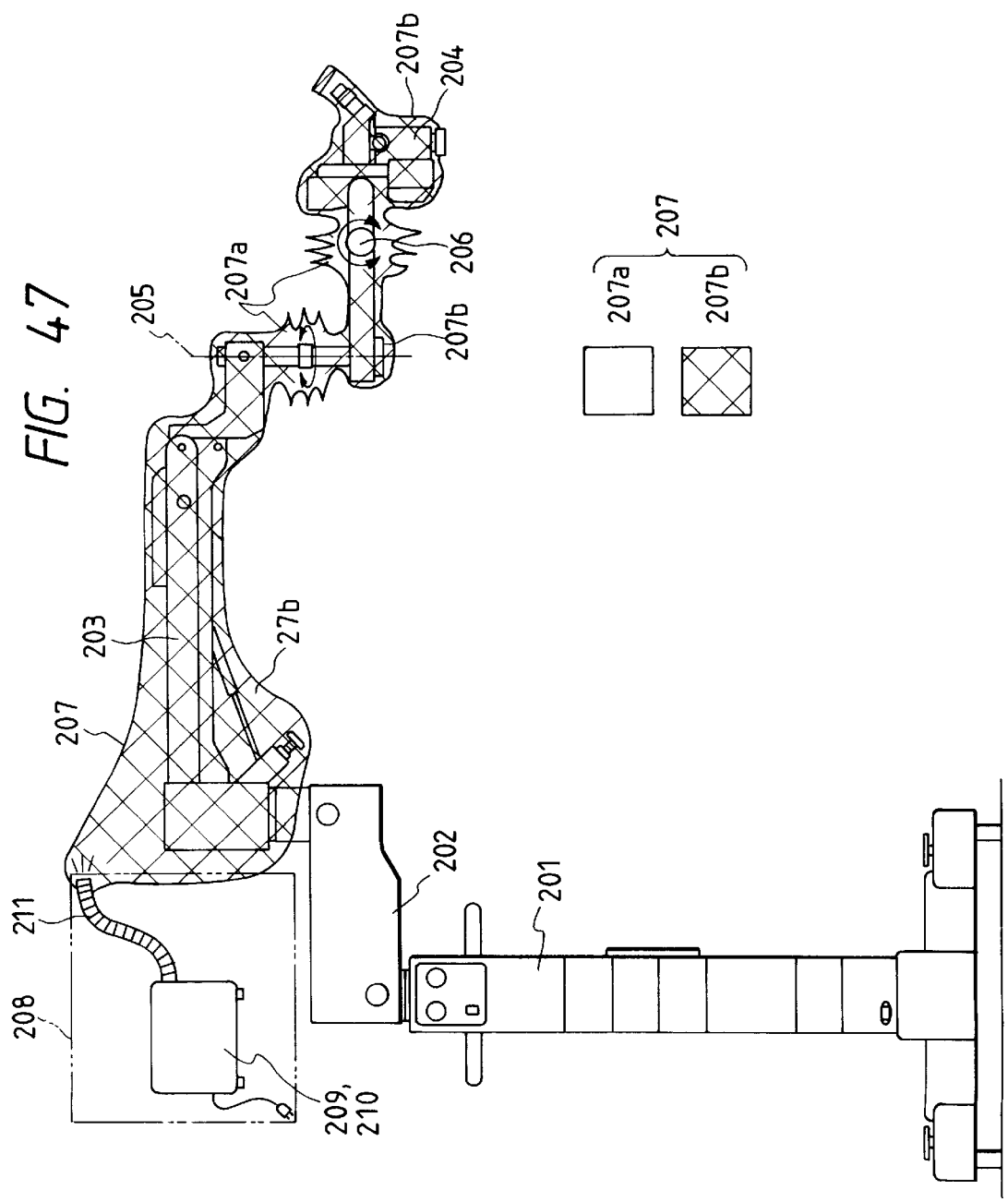
FIG. 47 shows the general layout of an eleventh embodiment of the invention.

FIG. 47 shows an eleventh embodiment of the invention. Reference numeral 201 refers to a stand having a built-in power supply; 202 is a first support arm that swivels in a horizontal plane about the axis through the stand; 203 is a second arm that swivels in a horizontal plane with respect to the first support arm 202; the second support arm 203 also pivots vertically through an angle of 60 degrees about an axis on the first support arm side, 30 degrees in each of UP and DOWN directions; 204 is the microscope body; 205 is a shaft about which the microscope body swivels horizontally; 206 is a shaft about which the microscope body pivots vertically; 207 is a sterile cover consisting of two portions 207a and 207b (207a corresponding to articulated parts such as shafts 205 and 206 which will move through a wide range and being formed of a non-heat shrinkable material, and 207b corresponding to the other parts of the microscope body and being formed of a heat shrinkable material such as a polyolefin or poly(vinylidene fluoride); and 208 is means for causing the sterile cover 207 to shrink, which contains a heater 209 and a fan 210 so that heated air can be blown through a pipe 211 into the sterile cover 207.

Before starting the surgical operation, the surgeon or an authorized operating staff member slips the sterile cover 207 over the microscope for operation including the first support arm 202, the second support arm 203 and the body 204. He then turns on the heating means 208 so that the air heated with heater 209 is forced with fan 21 to be blown into the sterile cover 207 through pipe 211. The supplied hot air shrinks only the part 207b of the sterile cover 207 that is formed of a heat shrinkable material, whereupon it makes intimate contact with the microscope body 204 as well as the first and second support arms 202 and 203. Since the part 207a of the sterile cover 207 which corresponds to articulated parts such as the shafts 205 and 206 in the microscope body 204 is formed of a non-heat shrinkable material, it has a sufficient allowance for those articulated parts to move through a wide range.

In the eleventh embodiment, the sterile cover 207 can be easily brought into intimate contact with the microscope for operation without taking the trouble of binding with strings or rubber bands. In addition, the cover as placed over the microscope does not have many loose portions that interfere with the vision of the surgeon. What is more, the part 207a of the sterile cover 207 which corresponds to the articulated parts of the microscope for operation that can move through a wide range does not shrink and there is no possibility for the manipulability of the articulated parts to be impaired by the tension of the sterile cover 207. The above description of the eleventh embodiment of the invention assumes that the heat shrinkable material is a synthetic resin such as a polyolefin or poly(vinylidene fluoride) but this is not the sole case of the invention and the sterile drape may be fabricated from a polyethylene or other substrate materials by incorporating a shape-memory alloy or a shape-memory resin mesh that have been so processed that they will shrink in a coil form upon beating. Other substituents for the heat shrinkable material are synthetic resins such as polypropylene and polysulfone; these substitute materials have the advantage of obviating the need to use the heating device. Whichever materials are used to form the part 207b, they must be capable of withstanding sterilization, which may appropriately be performed under superatmospheric pressures at temperatures higher than 100° C.

Figure 48:
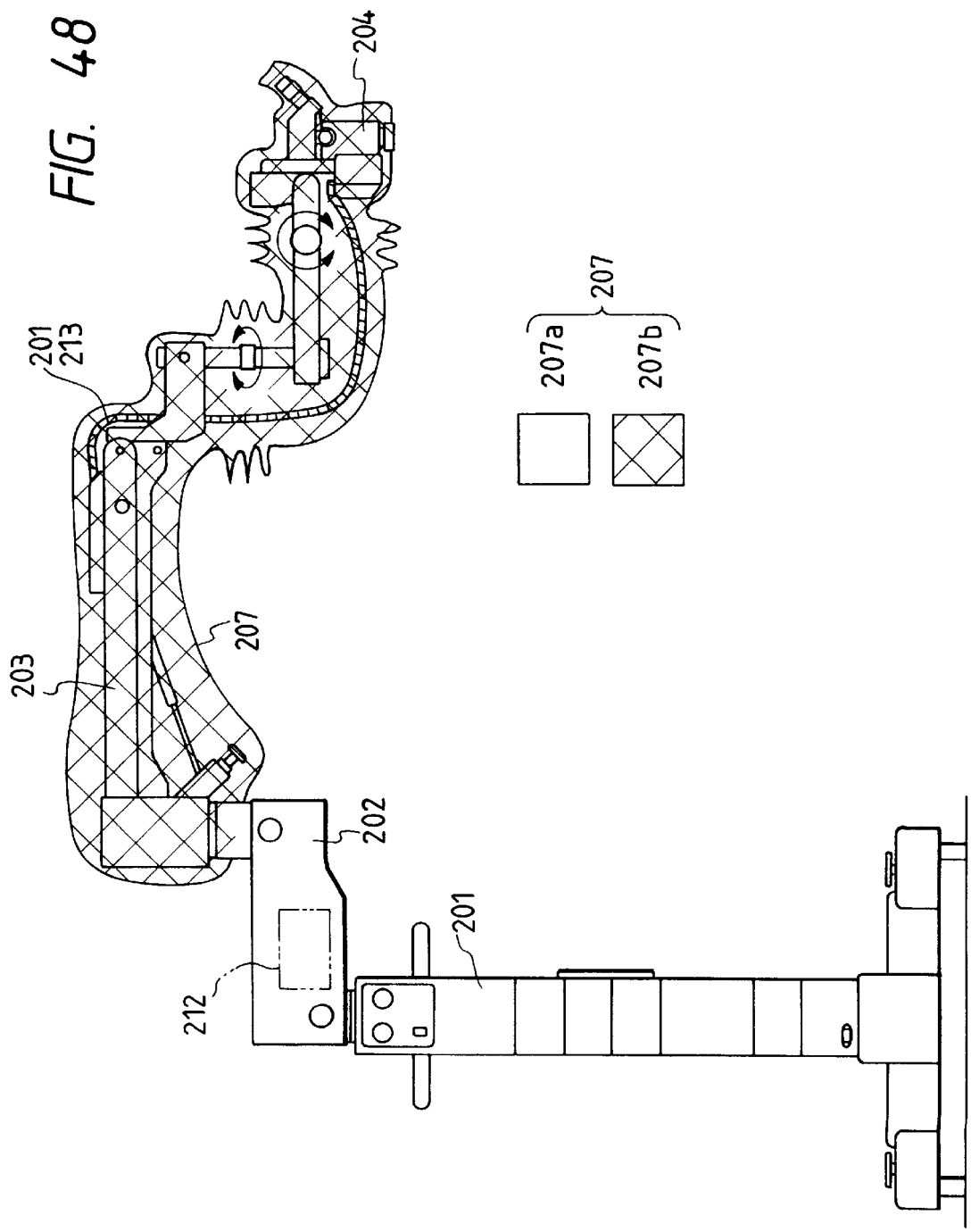
FIG. 48 shows the general layout of a twelfth embodiment of the invention.
Figure 49:
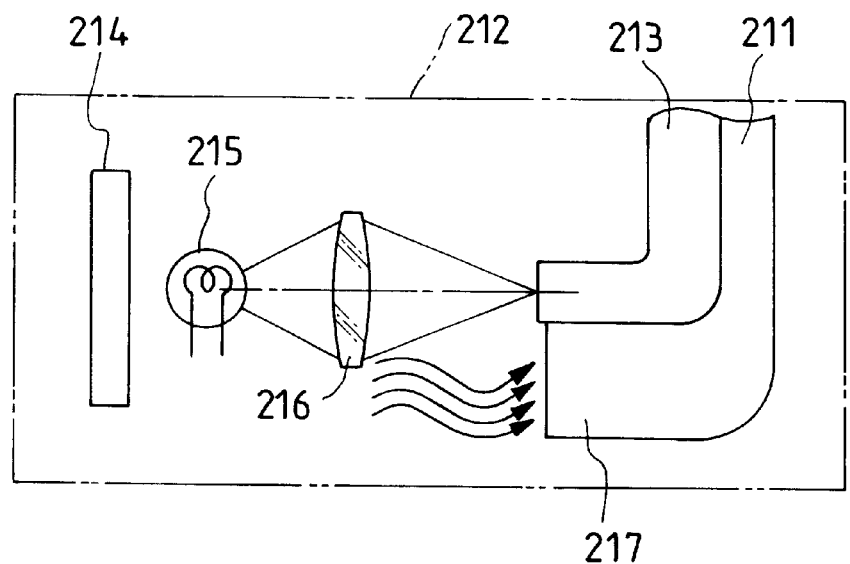
FIG. 49 is an enlarged view of the light source unit in the twelfth embodiment.

FIG. 48 shows the general layout of a twelfth embodiment; FIG. 49 is an enlarged view of the light source unit; and FIG. 50 is an enlarged view of the parts around the microscope body.

Referring to FIG. 48, numeral 212 designates the light source unit for illuminating the part of a patient under operation, which is contained in the first support arm 202; 213 is a lightguide that is formed as an integral part of the hot air supply pipe 211 and connected at one end to the microscope body 204, with the other end being connected to the light source unit 212 in the first support arm 202 after passage through the second support arm 203.

Referring to FIG. 49, numeral 214 designates a fan for cooling a light source 215 such as a halogen lamp; 216 is a condenser lens; and 217 is the inlet of air to the hot air supply pipe 211.

Figure 50:
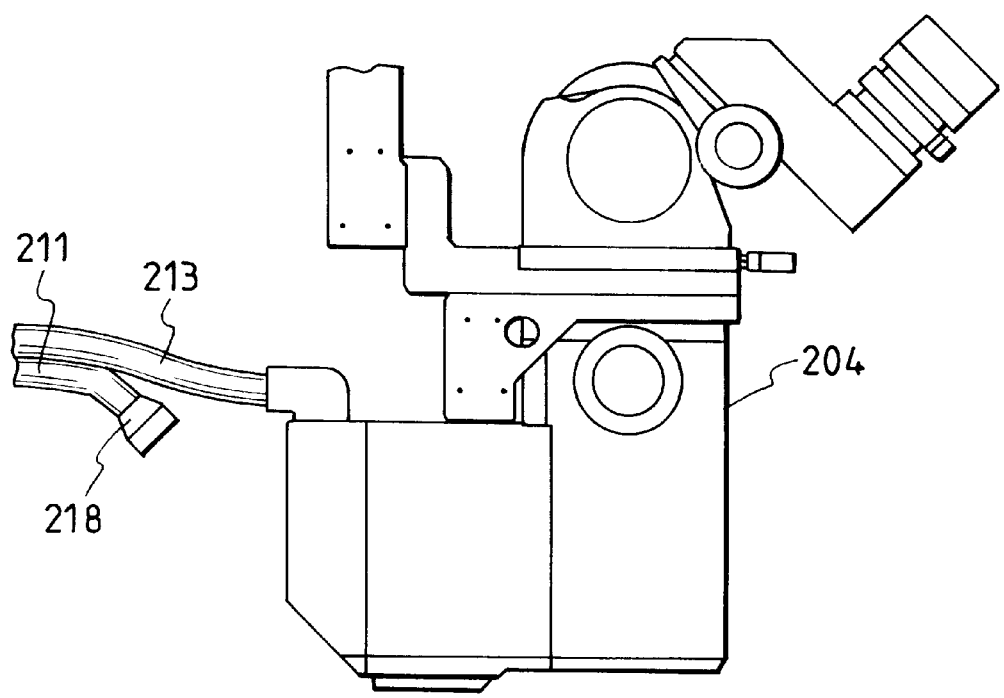
FIG. 50 is an enlarged view of the parts around the microscope for operation body.

Referring to FIG. 50, numeral 218 designates the outlet of air from the pipe 211.

Before starting the surgical operation, the surgeon or an authorized operating staff member slips the sterile heat-shrinkable cover 207 over the microscope for operation including the first support arm 202, the second support arm 203 and the body 204. He then turns on the fan 214 and the light source so that the air heated with the light source 215 is forced with fan 214 to be blown to the air inlet 217. The supplied hot air passes through the pipe 211 to be directed into the microscope body 204, thence emerges through the outlet 218, whereupon the sterile cover 207 shrinks in the area 207b formed of a heat-shrinkable material so that it is brought into intimate contact with the microscope body 204, as well as the first and second support arms 202 and 203.

In the twelfth embodiment, the sterile cover 207 can be easily brought into intimate contact with the microscope for operation without taking the trouble of binding with strings or rubber bands. In addition, the cover as placed over the microscope does not have many loose portions that interfere with the vision of the surgeon.

What is more, the part 207a of the sterile cover 207 which corresponds to the articulated parts of the microscope for operation that can move through a wide range does not shrink and there is no possibility for the manipulability of the articulated parts to be impaired by the tension of the sterile cover 207. Since the fan 214 and the light source 215 are in most cases contained in the microscope for operation, the concept of the invention can be embodied economically by simply equipping an existing microscope for operation with the hot air supply pipe 211.

The foregoing description of the twelfth embodiment assumes that the air outlet 218 of the pipe 211 is positioned near the microscope body 204 but this is not the sole case of the invention and the outlet 218 may be positioned in any areas. If desired, the hot air supply pipe 211 may have two or more outlets of air.

FIG. 51 shows the general layout of a thirteenth embodiment of the invention, and FIG. 52 shows in detail the structure of a heat generating unit.

In FIG. 51, reference numeral 219 designates a plurality of heat generating units that are fitted in the corresponding number of receptacles which are provided in selected areas such as the first support arm 202, the second support arm 203 and the microscope body 204; 221 is a control of the heat generating units; and 222 is a sterile cover generally made of a heat shrinkable material.

As shown in FIG. 52, each of the heat generating units 219 consists of a heat generating element 223 incorporating an electric heater, a connector portion 224 and a flexible hose 225 that connect these two members. The connector portion 224 is connectable to each receptor 220.

Before starting the surgical operation, the surgeon or an authorized operating staff member checks the ranges of movements of the arms that are determined by the type of surgical operation to be conducted. In accordance with the thus determined ranges of arm movements, connector portions 224 are connected to the receptacles 220 in the selected areas such as the first support arm 202, the second support arm 203 and the microscope body 204 and after bending the hoses 225 such as to adjust the directions and positions of the heat generating elements, the heat generating units 219 are set up. Subsequently, the heat-shrinkable sterile cover 222 is slipped over the microscope for operation including the first and second support arms 202 and 203, as well as the microscope body 204. By controlling the amount of heat generation from the units 219 through the control 221, the sterile cover 222 is allowed to shrink appropriately so that it is brought into intimate contact with the microscope body 204, as well as the first and second support arms 202 and 203.

In the thirteenth embodiment, the sterile cover 222 can be easily brought into intimate contact with the microscope for operation without taking the trouble of binding with strings or rubber bands. In addition, the cover as placed over the microscope does not have many loose portions that interfere with the vision of the surgeon. As a further advantage, the sterile cover 222 can generally be formed of a single material (heat shrinkable material), so not only can it be fabricated by a simple and inexpensive method but it can also be used satisfactorily even if there is a small change in the kind of accessory devices such as a TV camera which are to be attached to the microscope body 204. In addition to this broad range of applicability, any desired portions of the sterile cover can be adapted to be shrinkable such that it will be brought into intimate contact with only non-articulated areas of the microscope for operation, thereby ensuring against deterioration in the manipulability of the latter.

The foregoing description of the thirteenth embodiment assumes that the heat generating units 219 are adapted to be separable from the body of the microscope for operation but this is not the sole case of the invention and the heat generating units 219 may be provided as integral parts of the microscope for operation such that the sterile cover 22 is caused to shrink with the heat generated in selected areas under the control by the unit 221. Alternatively, the heat generating units 219 may be constructed to permit the blowing of heated air as in the eleventh and twelfth embodiments. If desired, the heat of chemical reaction may be utilized as a heat source for the heat generating units 219. This approach presents difficulty in controlling the amount of heat generation but, on the other hand, there is no need to provide the receptacles 220 and control unit 221 in association with the heat generating units and a system of a simple structure can be fabricated at a lower cost.

FIG. 53 shows the general layout of a fourteenth embodiment of the invention. A hose 225 is flexible and can be wound, unwound or rewound by a takeup unit 226 in the stand 201. The distal end of the hose 225 has a heat generating unit 223 with a built-in heater for heating selected areas such as the first support arm 202, the second support arm 203 and the microscope body 204. The heat generating unit 223 can be turned on or off and the amount of heat generation controlled by a control unit 221 contained in the stand 201.

Before starting the surgical operation, the surgeon or an authorized operating staff member slips the sterile cover 222 over the microscope for operation including the first and second support arms 202 and 203, as well as the microscope body 204. Then, the position of the heat generating unit 223 is adjusted by the hose 225 and the takeup unit 226 so as to provide access to any area of the sterile cover 222 that need be shrunk. The amount of heat generation from the heat generating unit 223 is adjusted by the control 221 and the non-articulated areas of the sterile cover 222 which need be shrunk are heated such that it is brought into intimate contact with the microscope body 204, as well as the first and second support arms 202 and 203.

After these preparatory steps, the hose 225 is rewound by the takeup unit 226 so that the heat generating unit 223 is contained in the stand 201.

In the fourteenth embodiment, the sterile cover 222 can be easily brought into intimate contact with the microscope for operation without taking the trouble of binding with strings or rubber bands. In addition, the cover as placed over the microscope body does not have many loose portions that interfere with the vision of the surgeon. As a further advantage, the sterile cover 221 can generally be formed of a single material (heat shrinkable material), so not only can it be fabricated by a simple and inexpensive method but it can also be used satisfactorily even if there is a small change in the kind of accessory devices such as a TV camera which are to be attached to the microscope body 204. In addition to this broad range of applicability, the areas to be shrunk and the degree of their shrinkage can be easily and freely adjusted even after the sterile cover 222 is placed over the microscope for operation and, hence, the cover can be brought into intimate contact with only non-articulated areas of the microscope for operation, thereby ensuring against deterioration its manipulability.

As a further advantage, there is no need to provide a heat generating unit in the microscope body 204 or the first or second support arm 203 or 204 or other parts of the microscope for operation and, hence, the latter can be constructed as a lighter and smaller system.

In the fourteenth embodiment, the heat generating unit 223 is provided at the distal end of the hose 225 extending from the stand 201. If desired, a construction similar to the one adopted in the twelfth embodiment may be provided such that the light source unit 212 in the first support arm 202 is used as a heat source for heating air that is supplied through the pipe 211 to be blown against the outer surface of the sterile cover 222 to shrink it. Alternatively, heating means similar to the one indicated by 208 in FIG. 47 (for the eleventh embodiment) may be provided as a separate member from the microscope for operation. If desired, such heating means 208 may be adapted to be supplied with power from a battery in the stand 201 so that there is no need to use noisome electric cables.

According to the 11th to 14th embodiments of the invention, there could be provided the following in addition to the recitations in appended claims.

11th Embodiment (1) A sterile cover for use on a microscope for operation which uses a heat shrinkable material in areas of small movements other than those corresponding to the articulated parts of the microscope for operation.

(2) A apparatus for shrinking a sterile cover over an microscope for operation which uses a heat shrinkable material in at least part of said cover, which is characterized by incorporating heating means for shrinking said cover.

(3) A microscope for operation incorporating the sterile cover shrinking apparatus recited in (2).

12th Embodiment (4) A microscope for operation as recited in (3), wherein an illuminating light source unit is used as a heat source for the heating means.

13th Embodiment (5) A microscope for operation as recited in (3), wherein the heating means can be set to generate heat at a desired site.

14th Embodiment (6) A microscope for operation as recited in (3), wherein the heating means generates heat in an area of the microscope that is not covered by the sterile cover and is adapted to be movable.

The advantages of the invention may be summarized as follows. First, the entire body of a microscope for operation can be easily rendered in a hostile condition. Second, a cap or caps can be easily mounted over the microscope body, so the time-consuming work in making preparations for a surgical operation can be eliminated. Third, the overall shape of the cover does not depend on the skill of the person who mounts the caps over the microscope body and, hence, consistency in the shape of the cover is insured. Fourth, the caps can be mounted without interfering with the manipulation of the microscope for operation and the vision of the surgeon.

What is claimed is:

1. A sterile instrument cover for covering an exterior of a surgical microscope having at least a main body portion, a moveable lens mount portion that is moveable relative to the main body portion, and a connecting portion between the moveable lens mount portion and the main body portion, the sterile instrument cover comprising:

a deformable portion for covering an exterior surface of the connecting portion of the microscope, the deformable portion conforming to movement of the moveable lens mount portion relative to the main body portion; and a non-deformable portion having upper and lower cap portions connected by the deformable portion for covering exterior surfaces of at least a part of the main body portion and at least a part of the moveable lens mount portion such that the main body portion is substantially contained within and covered by the lower cap portion, the moveable lens mount portion is substantially contained within and covered by the upper cap portion, and the deformable and non-deformable portions cover an entire exterior surface of the microscope.

2. The sterile instrument cover according to claim 1, wherein the deformable portion follows movement of the moveable lens mount portion of the microscope and wherein a diameter of an opening of the deformable member is variable.

3. The sterile instrument cover according to claim 1, wherein the deformable portion is disposed to face one of the main body and moveable lens mount portions of the microscope, and wherein the non-deformable portion is fixable to the main body portion of the microscope.

4. The sterile instrument cover according to claim 3, wherein the deformable and non-deformable portions are formed in a unitary assembly.

5. The sterile instrument cover according to claim 3, wherein the deformable portion is formed separately from the non-deformable portion.

6. The sterile instrument cover according to claim 5, wherein the non-deformable portion comprises a member for accommodating the deformable portion.

7. The sterile instrument cover according to claim 5, wherein the non-deformable portion comprises a portion for breaking the deformable portion.

8. The sterile instrument cover according to claim 1, wherein the non-deformable portion comprises a member, for retaining a surgical instrument.

9. The sterile instrument cover according to claim 1, wherein the deformable portion accommodates movements of at least one eye piece relative to an objective lens.

10. The sterile instrument cover according to claim 9, wherein the deformable portion accommodates movements corresponding to rotating shafts of the microscope.

11. The sterile instrument cover according to claim 1, wherein the non-deformable portion is made of a synthetic resin.

12. The sterile instrument cover according to claim 11, wherein the synthetic resin is capable of withstanding a sterilization process.

13. The sterile instrument cover according to claim 11, wherein the synthetic resin is polysulfone.

14. The sterile instrument cover according to claim 11, wherein the synthetic resin is polypropylene.

15. The sterile instrument cover according to claim 1, wherein the non-deformable portion is made of a hard material.

16. The sterile instrument cover according to claim 1, wherein the non-deformable portion is made partly of a hard material and partly of an elastic material.

17. The sterile instrument cover according to claim 16, wherein the elastic material includes bellows.

18. The sterile instrument cover according to claim 1, wherein at least one of the deformable portion and the non-deformable portion comprises an engaging member engageable with a mating section of the microscope.

19. The sterile instrument cover according to claim 18, wherein an engaging force of the engaging member to the mating section of the microscope is sufficient to hold the engaging member of the sterile instrument cover to the microscope even when the moveable lens mount portion of the microscope moves relative to the main body portion.

20. The sterile instrument cover according to claim 18, wherein the engaging member is formed of a material attracted to the mating section of the microscope by magnetism.

21. The sterile instrument cover according to claim 18, wherein the engaging member is formed of a metallic material.

22. The sterile instrument cover according to claim 18, wherein the engaging member comprises at least one mounting portion and the mating section of the microscope comprises a retaining portion which is engageable with the mounting portion of the engaging member.

23. The sterile instrument cover according to claim 1, wherein the deformable portion includes bellows.

24. The sterile instrument cover according to claim 1, wherein the sterile instrument cover is magnetically engaged to the microscope.

25. A method of placing a sterile instrument cover over an exterior of a surgical microscope having at least a main body portion, a moveable lens mount portion, and a connecting portion between the main body portion and the moveable lens mount portion, the method comprising the steps of:
   providing a sterile instrument cover having a deformable portion to conform to movement of the connecting portion of the microscope as the moveable lens mount portion of the microscope moves relative to the main body portion thereof, and a substantially non-deformable portion having upper and lower cap portions connected by the deformable portion to conform to exterior surfaces of both at least a part of the main body portion and at least a part of the moveable lens mount portion of the microscope;
   opening the sterile instrument cover and slipping the sterile instrument cover over the microscope; and
   fitting the sterile instrument cover on to the microscope such that an entire exterior surface of the microscope is covered by the deformable and non-deformable portions with the main body portion being substantially contained within and covered by the lower cap portion, and with the moveable lens mount portion being substantially contained within and covered by the upper cap portion.

26. The method according to claim 25, wherein the deformable and non-deformable portions are formed in a unitary assembly.

27. The method according to claim 25, wherein the deformable portion is formed separately from the non-deformable portion.

28. The method according to claim 27, wherein the deformable portion is made of an elastic member.

29. The method according to claim 27, wherein the non-deformable portion is made of a hard material.

30. The method according to claim 27, wherein the non-deformable portion is made partly of a hard material and partly of an elastic material.

31. The method according to claim 30, wherein the elastic material comprises bellows.

32. The method according to claim 25, wherein the non-deformable portion is made of a synthetic resin.

33. The method according to claim 32, wherein the non-deformable portion is made of polysulfone.

34. The method according to claim 32, wherein the non-deformable portion is made of polypropylene.

35. The method according to claim 25, wherein the deformable portion includes bellows.

36. A sterile instrument cover for covering an exterior of a surgical microscope having at least a main body portion, a moveable lens mount portion that is moveable relative to the main body portion, and a connecting portion between the moveable lens mount portion and the main body portion, the sterile instrument cover comprising:
   a deformable portion for covering an exterior surface of the connection portion while adaptably conforming to movement of the connecting portion of the microscope as the moveable lens mount portion of the microscope moves relative to the main body portion thereof; and
   a non-deformable portion having upper and lower cap portions connected by the deformable portion for covering exterior surfaces of at least a part of the main body portion and at least a part of the moveable lens mount portion of the microscope such that the main body portion is substantially contained within and covered by the lower cap portion, the moveable lens mount portion is substantially contained within and covered by the upper cap portion, and the deformable and non-deformable portions cover an entire exterior surface of the microscope, the non-deformable portion formed of a material capable of withstanding a sterilizing process.

37. The sterile instrument cover according to claim 36, wherein the non-deformable portion is made of a synthetic resin.

38. The sterile instrument cover according to claim 36, wherein the non-deformable portion is made of a hard material.

39. A sterile surgical microscope comprising:
   a microscope main body;
   a movable lens mount-portion that is movable relative to said main body;
   a connecting portion defined between said main body and said movable lens mount portion; and a cover member covering said microscope main body, said movable lens mount portion and said connecting portion, said cover member including:
  a deformable portion for adaptably conforming to an exterior surface of said connecting portion as said movable lens mount portion moves relative to said main body, said deformable portion conforming to follow the movement of said movable lens mount portion at said connecting portion, and
  a non-deformable portion having upper and lower cap portions connected by said deformable portion for conforming to entire exterior surfaces of both at least a part of said main body and at least a part of said movable lens mount portion, said non-deformable portion conforming to the exterior of said main body and the exterior of said movable lens mount portion,
  wherein the main body portion is substantially contained within and covered by the lower cap portion,
  wherein the moveable lens mount portion is substantially contained within and covered by the upper cap portion, and
  wherein said cover member covers the entire exterior surfaces of said main body, said movable lens mount portion, and said connecting portion.

40. The sterile surgical microscope of claim 39, wherein said main body comprises an objective lens and said movable lens mount portion comprises at least one eye-piece, said deformable portion adaptably conforms to follow the movement of said lens mount at said connecting portion.

41. A sterile surgical microscope comprising:
a main body;
a movable portion that is movable relative to said main body;
a connecting portion defined between said main body and said movable portion; and
a cover member covering said main body, said movable portion and said connecting portion, said cover member including:
  a deformable portion for adaptably conforming to movement of said connecting portion as said movable portion moves relative to said main body, said deformable portion adaptably conforming to follow the movement of said movable portion at said connecting portion, and
  a non-deformable portion including upper and lower cap portions for conforming to entire exterior surfaces of both at least a part of said main body and a part of said movable portion, said non-deformable portion conforming to the exterior of said main body and the exterior of said movable portion, said non-deformable portion being formed of a material capable of withstanding a sterilizing process,
  wherein the main body portion is substantially contained within and covered by the lower cap portion,
  wherein the moveable lens mount portion is substantially contained within and covered by the upper cap portion,
  wherein said cover member covers entire exterior surfaces of said main body, said movable portion, and said connecting portion, and
  wherein said cover member is divided into at least two parts.

42. The sterile surgical microscope of claim 41, wherein said main body comprises an objective lens and said movable portion comprises a lens mount to which at least one eye-piece is mounted, said deformable portion adaptably conforms to follow the movement of said lens mount at said connecting portion, and said non-deformable portion conforms to the exterior of said main body and the exterior of said lens mount.

43. A sterile instrument cover for covering an exterior of a surgical microscope having at least a main body portion, a moveable lens mount portion that is moveable relative to the main body portion, and a connecting portion between the moveable lens mount portion and the main body portion, the sterile instrument cover comprising:
a lower cap portion for fixedly conforming to an exterior surface of at least a part of the main body portion of the microscope such that the main body portion is substantially contained within and covered by the lower cap portion;
an upper cap portion for fixedly conforming to an exterior surface of at least a part of the moveable lens mount portion such that the moveable lens mount portion is substantially contained within and covered by the upper cap portion; and
a deformable portion for adaptably conforming to an exterior surface of the connecting portion of the microscope as the moveable lens mount portion moves relative to the main body portion, the deformable portion disposed to connect the lower and upper cap portions.

\* \* \* \* \*